(12) United States Patent
Keilman et al.

(10) Patent No.: US 8,226,629 B1
(45) Date of Patent: Jul. 24, 2012

(54) ULTRASONIC CATHETER POWER CONTROL

(75) Inventors: George Keilman, Woodinville, WA (US); Douglas R. Hansmann, Bainbridge Island, WA (US); Azita Soltani, Snohomish, WA (US); Richard R. Wilson, Seattle, WA (US)

(73) Assignee: Ekos Corporation, Bothell, WA (US)

( * ) Notice: Subject to any disclaimer, the term of this patent is extended or adjusted under 35 U.S.C. 154(b) by 59 days.

(21) Appl. No.: 12/415,965

(22) Filed: Mar. 31, 2009

Related U.S. Application Data

(62) Division of application No. 10/405,423, filed on Apr. 1, 2003, now abandoned.

(60) Provisional application No. 60/369,438, filed on Apr. 1, 2002.

(51) Int. Cl.
*A61M 31/00* (2006.01)
(52) U.S. Cl. .......................... 604/500; 604/20
(58) Field of Classification Search .............. 604/20–22, 604/500, 501
See application file for complete search history.

(56) References Cited

U.S. PATENT DOCUMENTS

| | | | |
|---|---|---|---|
| 2,961,382 A | 11/1960 | Singher et al. |
| 3,430,625 A | 3/1969 | McLeod, Jr. |
| 3,433,226 A | 3/1969 | Boyd |
| 3,565,062 A | 2/1971 | Kuris |
| 3,827,115 A | 8/1974 | Bom |
| 3,941,122 A | 3/1976 | Jones |
| 4,027,659 A | 6/1977 | Slingluff |
| 4,040,414 A | 8/1977 | Suroff |
| 4,192,294 A | 3/1980 | Gekhman et al. |
| 4,309,989 A | 1/1982 | Fahim |
| 4,319,580 A | 3/1982 | Colley |
| 4,354,502 A | 10/1982 | Colley |
| 4,466,442 A | 8/1984 | Hilmann et al. |
| 4,512,762 A | 4/1985 | Spears |
| 4,531,943 A | 7/1985 | Van Tassel |
| 4,573,470 A | 3/1986 | Samson et al. |
| 4,582,067 A | 4/1986 | Silverstein et al. |

(Continued)

FOREIGN PATENT DOCUMENTS

DE 39 19 592 A1 2/1990

(Continued)

OTHER PUBLICATIONS

Akhtar, *Anti-HIV therapy with antisense oligonucleotides and ribozymes: realistic approaches or expensive myths?* (J. Antimicrob Chemother. 38(2): 159-165, 1996).

(Continued)

*Primary Examiner* — Theodore Stigell
(74) *Attorney, Agent, or Firm* — Knobbe, Martens, Olson & Bear, LLP

(57) ABSTRACT

A method of treating an occlusion at a treatment site within a patient's vasculature comprises providing an ultrasonic catheter. The ultrasonic catheter has a distal region, a proximal region opposite the distal region, a fluid delivery lumen having at least one opening in the distal region, and an ultrasound radiating member positioned within the distal region. The method further comprises positioning the ultrasonic catheter at the treatment site, such that at least a portion of the distal region is within the occlusion. The ultrasonic catheter further comprises passing a therapeutic compound through the fluid delivery lumen such that the therapeutic compound is delivered to the treatment site. The ultrasonic catheter further comprises emitting ultrasonic energy from the ultrasound radiating member. The emitted ultrasonic energy has an amplitude that is periodically varied between a low amplitude and a high amplitude.

11 Claims, 18 Drawing Sheets

U.S. PATENT DOCUMENTS

| | | |
|---|---|---|
| 4,657,543 A | 4/1987 | Langer et al. |
| 4,657,756 A | 4/1987 | Rasor et al. |
| 4,692,139 A | 9/1987 | Stiles |
| 4,698,058 A | 10/1987 | Greenfeld et al. |
| 4,710,192 A | 12/1987 | Liotta et al. |
| 4,750,902 A | 6/1988 | Wuchinich |
| 4,754,752 A | 7/1988 | Ginsburg et al. |
| 4,762,915 A | 8/1988 | Kung et al. |
| 4,767,402 A | 8/1988 | Kost et al. |
| 4,772,594 A | 9/1988 | Hashimoto et al. |
| 4,774,958 A | 10/1988 | Feinstein |
| 4,780,212 A | 10/1988 | Kost et al. |
| 4,797,285 A | 1/1989 | Barenholz et al. |
| 4,808,153 A | 2/1989 | Parisi |
| 4,821,740 A | 4/1989 | Tachibana |
| 4,844,882 A | 7/1989 | Widder et al. |
| 4,870,953 A * | 10/1989 | DonMicheal et al. ........ 606/128 |
| 4,877,031 A | 10/1989 | Conway et al. |
| 4,900,540 A | 2/1990 | Ryan et al. |
| 4,917,088 A | 4/1990 | Crittendon |
| 4,917,102 A | 4/1990 | Miller et al. |
| 4,920,954 A | 5/1990 | Alliger |
| 4,921,478 A | 5/1990 | Solano et al. |
| 4,924,863 A | 5/1990 | Sterzer |
| 4,936,281 A | 6/1990 | Stasz |
| 4,948,587 A | 8/1990 | Kost et al. |
| 4,951,677 A | 8/1990 | Crowley et al. |
| 4,953,565 A | 9/1990 | Tachibana |
| 4,955,863 A | 9/1990 | Walker et al. |
| 4,960,109 A | 10/1990 | Lele |
| 4,971,991 A | 11/1990 | Umemura et al. |
| 4,992,257 A | 2/1991 | Bonnett et al. |
| 5,007,898 A | 4/1991 | Rosenbluth et al. |
| 5,021,044 A | 6/1991 | Sharkawy |
| 5,040,537 A | 8/1991 | Katakura |
| 5,053,044 A | 10/1991 | Mueller et al. |
| 5,059,851 A | 10/1991 | Corl et al. |
| 5,069,664 A | 12/1991 | Guess |
| 5,081,993 A | 1/1992 | Kitney |
| 5,085,662 A | 2/1992 | Willard |
| 5,088,499 A | 2/1992 | Unger |
| 5,117,831 A | 6/1992 | Jang et al. |
| 5,129,883 A | 7/1992 | Black |
| 5,149,319 A | 9/1992 | Unger |
| 5,156,050 A | 10/1992 | Schmid et al. |
| 5,158,071 A | 10/1992 | Umemura et al. |
| 5,163,421 A | 11/1992 | Bernstein |
| 5,178,620 A | 1/1993 | Eggers et al. |
| 5,181,920 A | 1/1993 | Mueller et al. |
| 5,185,071 A | 2/1993 | Serwer et al. |
| 5,190,766 A | 3/1993 | Ishihara |
| 5,197,946 A | 3/1993 | Tachibana |
| 5,209,720 A | 5/1993 | Unger |
| 5,215,680 A | 6/1993 | D'Arrigo |
| 5,216,130 A | 6/1993 | Line et al. |
| 5,226,421 A | 7/1993 | Frisbie et al. |
| 5,250,034 A | 10/1993 | Appling |
| 5,267,954 A | 12/1993 | Nita |
| 5,267,985 A | 12/1993 | Shimada |
| 5,269,291 A | 12/1993 | Carter |
| 5,269,297 A | 12/1993 | Weng et al. |
| 5,271,406 A | 12/1993 | Ganguly et al. |
| 5,277,913 A | 1/1994 | Thompson et al. |
| 5,279,546 A | 1/1994 | Mische et al. |
| 5,282,785 A | 2/1994 | Shapland et al. |
| 5,286,254 A | 2/1994 | Shapland |
| 5,295,484 A | 3/1994 | Marcus |
| 5,304,115 A | 4/1994 | Pflueger |
| 5,307,816 A | 5/1994 | Hashimoto |
| 5,312,328 A | 5/1994 | Nita et al. |
| 5,313,949 A | 5/1994 | Yock |
| 5,315,998 A | 5/1994 | Tachibana et al. |
| 5,318,014 A | 6/1994 | Carter |
| 5,323,769 A | 6/1994 | Bommannan |
| 5,324,255 A | 6/1994 | Passafaro et al. |
| 5,327,891 A | 7/1994 | Rammler |
| 5,328,470 A | 7/1994 | Nabel |
| 5,342,292 A | 8/1994 | Nita et al. |
| 5,344,395 A | 9/1994 | Whalen et al. |
| 5,344,435 A | 9/1994 | Turner |
| 5,345,940 A | 9/1994 | Seward et al. |
| 5,351,693 A | 10/1994 | Taimisto et al. |
| 5,353,798 A | 10/1994 | Sieben |
| 5,354,279 A | 10/1994 | Hofling |
| 5,362,309 A | 11/1994 | Carter |
| 5,363,853 A | 11/1994 | Lieber |
| 5,368,036 A | 11/1994 | Tanaka et al. |
| 5,368,557 A | 11/1994 | Nita |
| 5,368,558 A | 11/1994 | Nita |
| 5,370,675 A | 12/1994 | Edwards |
| 5,372,138 A | 12/1994 | Crowley et al. |
| 5,380,273 A | 1/1995 | Dubrul et al. |
| 5,390,678 A | 2/1995 | Gesswein |
| 5,397,293 A | 3/1995 | Alliger |
| 5,399,158 A | 3/1995 | Lauer et al. |
| 5,401,237 A | 3/1995 | Tachibana et al. |
| 5,405,322 A | 4/1995 | Lennox et al. |
| 5,415,636 A | 5/1995 | Forman |
| 5,419,763 A | 5/1995 | Hildebrand |
| 5,421,338 A | 6/1995 | Crowley et al. |
| 5,423,797 A | 6/1995 | Adrian et al. |
| 5,431,663 A | 7/1995 | Carter |
| 5,440,914 A | 8/1995 | Tachibana et al. |
| 5,445,155 A | 8/1995 | Sieben |
| 5,447,509 A | 9/1995 | Mills et al. |
| 5,447,510 A | 9/1995 | Jensen |
| 5,453,575 A | 9/1995 | O'Donell et al. |
| 5,456,259 A | 10/1995 | Barlow |
| 5,458,568 A | 10/1995 | Racchini et al. |
| 5,462,523 A | 10/1995 | Samson |
| 5,465,726 A | 11/1995 | Dickinson |
| 5,474,530 A | 12/1995 | Passafaro |
| 5,474,531 A | 12/1995 | Carter |
| 5,489,279 A | 2/1996 | Meserol |
| 5,498,238 A | 3/1996 | Shapland |
| 5,509,896 A | 4/1996 | Carter |
| 5,514,092 A | 5/1996 | Forman |
| 5,520,189 A | 5/1996 | Malinowski |
| 5,523,058 A | 6/1996 | Umemura et al. |
| 5,533,986 A | 7/1996 | Mottola et al. |
| 5,542,917 A | 8/1996 | Nita et al. |
| 5,542,935 A | 8/1996 | Unger et al. |
| 5,558,092 A | 9/1996 | Unger et al. |
| 5,558,642 A | 9/1996 | Schweich, Jr. et al. |
| 5,562,608 A | 10/1996 | Sekins |
| 5,567,687 A | 10/1996 | Magda et al. |
| 5,569,197 A | 10/1996 | Helmus et al. |
| 5,569,198 A | 10/1996 | Racchini |
| 5,580,575 A | 12/1996 | Unger et al. |
| 5,582,586 A | 12/1996 | Tachibana et al. |
| 5,585,112 A | 12/1996 | Unger et al. |
| 5,586,982 A | 12/1996 | Abela |
| 5,588,432 A | 12/1996 | Crowley |
| 5,588,962 A | 12/1996 | Nicholas et al. |
| 5,594,136 A | 1/1997 | Sessler et al. |
| 5,599,923 A | 2/1997 | Sessler et al. |
| 5,603,327 A | 2/1997 | Eberle |
| 5,603,694 A | 2/1997 | Brown et al. |
| 5,606,974 A | 3/1997 | Castellano |
| 5,609,574 A | 3/1997 | Kaplan et al. |
| 5,616,342 A | 4/1997 | Lyons |
| 5,617,851 A | 4/1997 | Lipkovker |
| 5,618,275 A | 4/1997 | Bock |
| 5,620,479 A | 4/1997 | Diederich |
| 5,624,382 A | 4/1997 | Oppelt |
| 5,628,728 A | 5/1997 | Tachibana et al. |
| 5,628,730 A | 5/1997 | Shapland |
| 5,630,837 A | 5/1997 | Crowley |
| 5,632,970 A | 5/1997 | Sessler et al. |
| 5,648,098 A | 7/1997 | Porter |
| 5,656,016 A | 8/1997 | Ogden |
| 5,660,180 A | 8/1997 | Malinowski |
| 5,660,909 A | 8/1997 | Tachibana et al. |
| 5,663,327 A | 9/1997 | Tambo et al. |
| 5,665,076 A | 9/1997 | Roth |
| 5,695,460 A | 12/1997 | Siegel et al. |
| 5,697,897 A | 12/1997 | Buchholtz et al. |

| Patent | Date | Name |
|---|---|---|
| 5,707,608 A | 1/1998 | Liu |
| 5,713,831 A | 2/1998 | Olsson |
| 5,713,848 A | 2/1998 | Dubrul et al. |
| 5,718,921 A | 2/1998 | Mathiowitz et al. |
| 5,720,710 A | 2/1998 | Tachibana et al. |
| 5,725,494 A * | 3/1998 | Brisken ............ 604/22 |
| 5,728,062 A | 3/1998 | Brisken |
| 5,733,315 A | 3/1998 | Burdette et al. |
| 5,733,572 A | 3/1998 | Unger et al. |
| 5,735,811 A | 4/1998 | Brisken |
| 5,766,902 A | 6/1998 | Craig et al. |
| 5,770,222 A | 6/1998 | Unger et al. |
| 5,772,632 A | 6/1998 | Forman |
| 5,775,338 A | 7/1998 | Hasting |
| 5,776,429 A | 7/1998 | Unger et al. |
| 5,779,673 A | 7/1998 | Roth |
| 5,800,421 A | 9/1998 | Lemelson |
| 5,817,021 A | 10/1998 | Reichenberger |
| 5,817,048 A | 10/1998 | Lawandy |
| 5,827,203 A | 10/1998 | Nita |
| 5,836,896 A | 11/1998 | Rosenschein |
| 5,836,940 A | 11/1998 | Gregory |
| 5,840,031 A | 11/1998 | Crowley |
| 5,846,218 A | 12/1998 | Brisken et al. |
| 5,849,727 A | 12/1998 | Porter et al. |
| 5,876,345 A | 3/1999 | Eaton |
| 5,876,989 A | 3/1999 | Berg et al. |
| 5,895,356 A | 4/1999 | Andrus |
| 5,895,398 A | 4/1999 | Wensel et al. |
| 5,916,192 A | 6/1999 | Nita et al. |
| 5,922,687 A | 7/1999 | Mann et al. |
| 5,925,016 A | 7/1999 | Chornenky et al. |
| 5,928,186 A | 7/1999 | Homsma et al. |
| 5,931,805 A | 8/1999 | Brisken |
| 5,935,124 A | 8/1999 | Klumb et al. |
| 5,938,595 A | 8/1999 | Glass et al. |
| 5,941,868 A | 8/1999 | Kaplan et al. |
| 5,957,882 A | 9/1999 | Nita et al. |
| 5,957,941 A | 9/1999 | Ream |
| 5,971,949 A | 10/1999 | Levin et al. |
| 5,976,120 A | 11/1999 | Chow et al. |
| 5,997,497 A | 12/1999 | Nita et al. |
| 6,001,069 A | 12/1999 | Tachibana et al. |
| 6,004,269 A | 12/1999 | Crowley et al. |
| 6,024,718 A | 2/2000 | Chen et al. |
| 6,027,515 A | 2/2000 | Cimino |
| 6,030,374 A | 2/2000 | McDaniel |
| 6,033,397 A | 3/2000 | Laufer et al. |
| 6,053,868 A | 4/2000 | Geistert et al. |
| 6,059,731 A | 5/2000 | Seward |
| 6,063,069 A | 5/2000 | Cragg |
| 6,068,857 A | 5/2000 | Weitschies et al. |
| 6,078,830 A | 6/2000 | Levin et al. |
| 6,086,573 A | 7/2000 | Siegel |
| 6,088,613 A | 7/2000 | Unger |
| 6,089,573 A | 7/2000 | Udagawa |
| 6,096,000 A | 8/2000 | Tachibana et al. |
| 6,096,070 A | 8/2000 | Ragheb et al. |
| 6,110,098 A | 8/2000 | Renirie et al. |
| 6,110,314 A | 8/2000 | Nix et al. |
| 6,113,546 A | 9/2000 | Suorsa et al. |
| 6,113,558 A | 9/2000 | Rosenschein et al. |
| 6,113,570 A | 9/2000 | Siegel et al. |
| 6,117,101 A | 9/2000 | Diederich et al. |
| 6,117,858 A | 9/2000 | Porter et al. |
| 6,120,454 A | 9/2000 | Suorsa et al. |
| 6,135,971 A | 10/2000 | Hutchinson et al. |
| 6,135,976 A | 10/2000 | Tachibana |
| 6,149,599 A | 11/2000 | Schlesinger |
| 6,176,842 B1 | 1/2001 | Tachibana et al. |
| 6,190,355 B1 | 2/2001 | Hastings |
| 6,196,973 B1 | 3/2001 | Lazenby et al. |
| 6,206,831 B1 | 3/2001 | Suorsa |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,231,516 B1 | 5/2001 | Keilman et al. |
| 6,235,024 B1 | 5/2001 | Tu |
| 6,238,347 B1 | 5/2001 | Nix et al. |
| 6,245,747 B1 | 6/2001 | Porter et al. |
| 6,261,246 B1 | 7/2001 | Pantages |
| 6,277,077 B1 | 8/2001 | Brisken et al. |
| 6,283,920 B1 | 9/2001 | Eberle |
| 6,287,271 B1 | 9/2001 | Dubrul et al. |
| 6,295,990 B1 | 10/2001 | Lewis et al. |
| 6,296,619 B1 | 10/2001 | Brisken et al. |
| 6,299,597 B1 | 10/2001 | Buscemi et al. |
| 6,309,370 B1 | 10/2001 | Haim et al. |
| 6,312,402 B1 | 11/2001 | Hansmann |
| 6,346,098 B1 | 2/2002 | Yock et al. |
| 6,361,500 B1 | 3/2002 | Masters |
| 6,361,554 B1 | 3/2002 | Brisken |
| 6,366,719 B1 | 4/2002 | Heath et al. |
| 6,372,498 B2 | 4/2002 | Newman et al. |
| 6,387,052 B1 | 5/2002 | Quinn et al. |
| 6,391,042 B1 | 5/2002 | Cimino |
| 6,394,997 B1 | 5/2002 | Lemelson |
| 6,416,740 B1 | 7/2002 | Unger |
| 6,423,026 B1 | 7/2002 | Gesswein et al. |
| 6,425,853 B1 | 7/2002 | Edwards |
| 6,433,464 B2 | 8/2002 | Jones |
| 6,437,487 B1 | 8/2002 | Mohr, III et al. |
| 6,456,863 B1 | 9/2002 | Levin |
| 6,461,296 B1 | 10/2002 | Desai |
| 6,461,383 B1 | 10/2002 | Gesswein et al. |
| 6,461,586 B1 | 10/2002 | Unger |
| 6,464,680 B1 | 10/2002 | Brisken et al. |
| 6,485,430 B1 | 11/2002 | Quinn |
| 6,503,202 B1 | 1/2003 | Hossack et al. |
| 6,506,584 B1 | 1/2003 | Chandler et al. |
| 6,508,775 B2 | 1/2003 | McKenzie et al. |
| 6,508,816 B2 | 1/2003 | Shadduck |
| 6,511,478 B1 | 1/2003 | Burnside et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,527,761 B1 | 3/2003 | Soltesz et al. |
| 6,537,224 B2 | 3/2003 | Mauchamp et al. |
| 6,542,767 B1 | 4/2003 | McNichols et al. |
| 6,548,047 B1 | 4/2003 | Unger |
| 6,551,337 B1 | 4/2003 | Rabiner et al. |
| 6,561,998 B1 | 5/2003 | Roth |
| 6,562,021 B1 | 5/2003 | Derbin et al. |
| 6,575,922 B1 | 6/2003 | Fearnside et al. |
| 6,575,956 B1 | 6/2003 | Brisken et al. |
| 6,579,277 B1 | 6/2003 | Rabiner et al. |
| 6,579,279 B1 | 6/2003 | Rabiner |
| 6,582,392 B1 | 6/2003 | Bennett et al. |
| 6,585,763 B1 | 7/2003 | Keilman |
| 6,589,182 B1 | 7/2003 | Loftman et al. |
| 6,599,288 B2 | 7/2003 | Maguire |
| 6,605,084 B2 | 8/2003 | Acker et al. |
| 6,607,502 B1 | 8/2003 | Maguire et al. |
| 6,635,017 B1 | 10/2003 | Moehring et al. |
| 6,647,755 B2 | 11/2003 | Rabiner et al. |
| 6,652,547 B2 | 11/2003 | Rabiner et al. |
| 6,652,581 B1 | 11/2003 | Ding |
| 6,660,013 B2 | 12/2003 | Rabiner |
| 6,663,613 B1 | 12/2003 | Evans et al. |
| 6,676,626 B1 | 1/2004 | Bennett et al. |
| 6,680,301 B2 | 1/2004 | Berg et al. |
| 6,695,781 B2 | 2/2004 | Rabiner et al. |
| 6,723,063 B1 | 4/2004 | Zhang et al. |
| 6,726,698 B2 | 4/2004 | Cimino |
| 6,730,048 B1 | 5/2004 | Hare et al. |
| 6,733,450 B1 | 5/2004 | Alexandrov et al. |
| 6,733,451 B2 | 5/2004 | Rabiner et al. |
| 6,740,040 B1 | 5/2004 | Mandrusov et al. |
| 6,758,857 B2 | 7/2004 | Cioanta |
| 6,794,369 B2 | 9/2004 | Newman et al. |
| 6,797,293 B2 | 9/2004 | Shin et al. |
| 6,824,575 B1 | 11/2004 | Otomo et al. |
| 6,855,123 B2 | 2/2005 | Nita |
| 6,921,371 B2 | 7/2005 | Wilson |
| 6,929,633 B2 | 8/2005 | Evans et al. |
| 6,942,620 B2 | 9/2005 | Nita et al. |
| 6,958,040 B2 | 10/2005 | Oliver et al. |

| | | | |
|---|---|---|---|
| 6,958,059 B2 | 10/2005 | Zadno-Azizi | |
| 6,979,293 B2 * | 12/2005 | Hansmann et al. ........... 600/439 | |
| 7,077,820 B1 | 7/2006 | Kadziauskas et al. | |
| 7,141,044 B2 | 11/2006 | Gentsler | |
| 7,220,239 B2 | 5/2007 | Wilson et al. | |
| 7,341,569 B2 | 3/2008 | Soltani et al. | |
| 7,344,509 B2 | 3/2008 | Hynynen et al. | |
| 7,771,372 B2 | 8/2010 | Wilson | |
| 2001/0000791 A1 | 5/2001 | Suorsa | |
| 2001/0003790 A1 | 6/2001 | Ben-Haim et al. | |
| 2001/0007666 A1 | 7/2001 | Hoffman et al. | |
| 2001/0007861 A1 | 7/2001 | Newman | |
| 2001/0037106 A1 | 11/2001 | Shadduck | |
| 2001/0039419 A1 | 11/2001 | Francischelli et al. | |
| 2001/0041842 A1 | 11/2001 | Eberle | |
| 2001/0041880 A1 | 11/2001 | Brisken | |
| 2001/0053384 A1 | 12/2001 | Greenleaf et al. | |
| 2002/0000763 A1 | 1/2002 | Jones | |
| 2002/0019644 A1 | 2/2002 | Hastings | |
| 2002/0032394 A1 | 3/2002 | Brisken et al. | |
| 2002/0040184 A1 | 4/2002 | Brown | |
| 2002/0045890 A1 | 4/2002 | Celliers et al. | |
| 2002/0055731 A1 | 5/2002 | Atala et al. | |
| 2002/0068717 A1 | 6/2002 | Borrelli | |
| 2002/0068869 A1 | 6/2002 | Brisken et al. | |
| 2002/0077550 A1 | 6/2002 | Rabiner et al. | |
| 2002/0087083 A1 | 7/2002 | Nix | |
| 2002/0133111 A1 | 9/2002 | Shadduk | |
| 2002/0151792 A1 | 10/2002 | Conston et al. | |
| 2003/0036705 A1 | 2/2003 | Hare et al. | |
| 2003/0040501 A1 | 2/2003 | Newman et al. | |
| 2003/0069525 A1 | 4/2003 | Brisken et al. | |
| 2003/0220568 A1 | 11/2003 | Hansmann et al. | |
| 2004/0001809 A1 | 1/2004 | Brisken et al. | |
| 2004/0019318 A1 | 1/2004 | Wilson et al. | |
| 2004/0024347 A1 | 2/2004 | Wilson et al. | |
| 2004/0024393 A1 | 2/2004 | Nita et al. | |
| 2004/0039311 A1 | 2/2004 | Nita et al. | |
| 2004/0039329 A1 | 2/2004 | Ueberle | |
| 2004/0049148 A1 | 3/2004 | Rodriguez et al. | |
| 2004/0068189 A1 | 4/2004 | Wilson et al. | |
| 2004/0106841 A1 | 6/2004 | Shaw et al. | |
| 2004/0138570 A1 | 7/2004 | Nita et al. | |
| 2004/0162571 A1 | 8/2004 | Rabiner et al. | |
| 2004/0210134 A1 | 10/2004 | Hynynen et al. | |
| 2004/0243062 A1 | 12/2004 | Henry | |
| 2005/0027247 A1 | 2/2005 | Carrison et al. | |
| 2005/0043629 A1 | 2/2005 | Rabiner et al. | |
| 2005/0043753 A1 | 2/2005 | Rabiner et al. | |
| 2005/0054971 A1 | 3/2005 | Steen et al. | |
| 2005/0096669 A1 | 5/2005 | Rabiner et al. | |
| 2005/0113688 A1 | 5/2005 | Nita et al. | |
| 2005/0119679 A1 | 6/2005 | Rabiner et al. | |
| 2005/0124877 A1 | 6/2005 | Nita et al. | |
| 2005/0137520 A1 | 6/2005 | Rule et al. | |
| 2005/0187513 A1 | 8/2005 | Rabiner et al. | |
| 2005/0187514 A1 | 8/2005 | Rabiner et al. | |
| 2005/0197619 A1 | 9/2005 | Rule et al. | |
| 2005/0209578 A1 | 9/2005 | Evans et al. | |
| 2005/0215942 A1 | 9/2005 | Abrahamson et al. | |
| 2005/0215946 A1 | 9/2005 | Hansmann et al. | |
| 2006/0116610 A1 | 6/2006 | Hare et al. | |
| 2006/0173387 A1 | 8/2006 | Hansmann et al. | |
| 2007/0265560 A1 | 11/2007 | Soltani et al. | |
| 2008/0171965 A1 | 7/2008 | Soltani et al. | |
| 2008/0319376 A1 | 12/2008 | Wilcox et al. | |
| 2009/0018472 A1 | 1/2009 | Soltani et al. | |
| 2011/0004105 A1 | 1/2011 | Soltani et al. | |
| 2011/0301506 A1 | 12/2011 | Volz | |

FOREIGN PATENT DOCUMENTS

| | | |
|---|---|---|
| DE | 40 05 743 | 8/1991 |
| EP | 0 189 329 | 7/1986 |
| EP | 0 529 675 | 8/1992 |
| EP | 0 629 382 | 11/1993 |
| EP | 668052 A2 | 2/1995 |
| EP | 0744189 | 11/1996 |
| EP | 0 746 245 | 12/1996 |
| EP | 1090658 | 4/2001 |
| EP | 1 252 885 | 10/2002 |
| JP | 2-180275 | 7/1990 |
| WO | WO 89/05160 | 6/1989 |
| WO | WO 91/09629 | 7/1991 |
| WO | WO 92/00113 | 1/1992 |
| WO | WO 92/07622 | 5/1992 |
| WO | WO 93/08738 | 5/1993 |
| WO | WO 94/05361 | 3/1994 |
| WO | WO 95/01751 | 1/1995 |
| WO | WO 95/05866 | 3/1995 |
| WO | WO 95/09572 | 4/1995 |
| WO | WO 95/15118 | 6/1995 |
| WO | WO 96/04955 | 2/1996 |
| WO | WO 96/07432 | 3/1996 |
| WO | WO 96/15815 | 5/1996 |
| WO | WO 96/27341 | 9/1996 |
| WO | WO 96/29935 | 10/1996 |
| WO | WO 96/35469 | 11/1996 |
| WO | WO 96/36286 | 11/1996 |
| WO | WO 96/39079 | 12/1996 |
| WO | WO 97/19645 | 6/1997 |
| WO | WO 98/11826 | 3/1998 |
| WO | WO 89/04142 | 5/1998 |
| WO | WO 98/18391 | 5/1998 |
| WO | WO 98/48711 | 11/1998 |
| WO | WO 98/58699 | 12/1998 |
| WO | WO 99/16360 | 4/1999 |
| WO | WO 99/25385 | 5/1999 |
| WO | WO 99/33500 | 7/1999 |
| WO | WO 99/34858 | 7/1999 |
| WO | WO 99/39647 | 8/1999 |
| WO | WO 99/39738 | 8/1999 |
| WO | WO 99/42039 | 8/1999 |
| WO | WO 99/44512 | 9/1999 |
| WO | WO 00/00095 | 1/2000 |
| WO | WO 00/38580 | 7/2000 |
| WO | WO 00/69341 | 11/2000 |
| WO | WO 01/87174 | 11/2001 |
| WO | WO 01/95788 | 12/2001 |
| WO | WO 02/13678 | 2/2002 |
| WO | WO 02/15803 | 2/2002 |
| WO | WO 02/15804 | 2/2002 |
| WO | WO 03/007649 | 1/2003 |
| WO | WO 03/051208 | 6/2003 |
| WO | WO 2005/027756 | 3/2005 |
| WO | WO 2005/084552 | 9/2005 |
| WO | WO 2005/084553 | 9/2005 |
| WO | WO 2009/079415 | 6/2009 |
| WO | WO 2010/003130 | 1/2010 |
| WO | WO 2011/003031 | 1/2011 |

OTHER PUBLICATIONS

Anderson, *Human gene therapy*. (Nature 392:25-30, 1998).
B.D. Butler, J. clin. Ultrasound 14(5): 408-12 (Jun. 1986) Production of Microbubbles for Use as Echo Contrast Agents*.
Bao, et al. "Transfection of a Reporter Plasmid into Cultured Cells by Sonoporation In Vitro," Ultrasound in Med. and Biol., vol. 23, No. 6, pp. 953-.
Bleeker et al., J. Ultrasound, Med. 9(8): 461-71 (Aug. 1990) On the Application of Ultrsonic Contrast Agents for Blood Flowmetry and Assessment of Cardiac Perfusion*.
Branch, *A Good Antisense Molecule is Hard to Find*, (Trends in Biochem Sci 23: 45-50, 1998).
Cancer Letters, vol. 72, 1993, pp. 195-199.
Cancer Letters, vol. 78 (1-3), 1994, pp. 177-181.
U.S. Appl. No. 10/291,890, filed Nov. 7, 2002.
Crooke, *Basic Principles of Antisense Therapeutics* (Springer-Verlag, Eds, New York, 1998, pp. 1 and 4).
Fechmeier, et al. "Transfection of Mammalian Cells with Plasid DNA by Scrape Loading and Sonication Loading," Proc. Natl. Acad. Sci. USA, vol. 84, pp. 8463-8467, Dec. 1987.
Feinstein et al., J. Am. Coll. Cardiol. 3(1): 14-20 (Jan. 1984) Two-dimensional Contrast Echocardiography I. In Vitrro Development and Quantitative Analysis of Echo Contrast Agents*.
Feldman, et al. "Optimal Techniques for Arterial Gene Transfer," Cardiovascular Research, 35 (1997) pp. 391-404.

G. Maywald et al., "Experience With Atraumatic Vascular Diagnosis With the Aid of the Ultrasonic Doppler Technique", Electromedica, vol. 2 pp. 43-48 (1976).

Greenleaf, William J. et al.; Artifical Cavitation Nuclei Significantly Enhance Accoustically Induced Cell Transfection. vol. 24, No. 4 pp. 587-595, 1998.

Ho and Parkinson, *Antisense Oigonucleoties and Therapeutics for Malignant Diseases*, (Seminars in Drug Discovery 24(2): 187-202, 1997).

Holland, C.K. and R.E. Apfel, J. Acoust. Soc. Am. 88(5): 2059-2069 (Nov. 1990) Thresholds for Transient Cavitation Produced by Pulsed Ultrsound in a Controlled Nuclei Environment*.

Hynynen et al.; "Small Cylindrical Ultrasound Sources for Induction of Hyperthermia Via Body Cavities or Interstitial Implants", Arizona Cancer Center and Department of Radiation Oncology, University of Arizona Health Sciences Center; vol. 9, No. 2; pp. 263-274; 1993.

Japanese Journal of Cancer Research, vol. 81, No. 3, Mar. 1990, pp. 304-308.

Jeffers, R.J. et al.; Evaluation of the Effect of Cavitation Activity on Drug-Ultrsound Synergisms, 1993.

Jeffers, Russel et al; Dimethylformamide as an Enhancer of Cavitation-Induced Cell Lysis In Vitro, vol. 97, No. 1, Jan. 1995.

Keller et al., J. Ultrasound Med. 5(9): 493-8 (Sep. 1986) Automated Production and Analysis of Echo Contrast Agents*.

Kim, et al. "Ultra-sound Mediated Transfection of Mammalian Cells," Human Gene Therapy, 7: 1339-1346 (Jul. 10, 1996).

Kim, T.F. Medical news & Perspectives, JAMA 261(11): 1542 (Mar. 17, 1989) Microbubbles Show Promise for Enhancing Ultrasound Signal, Image, Other Applications*.

Kotnis, et al. "Optimisation of Gene Transfer into Vascular Endothelial Cells Using Electroporation," Eur J. Vasc Surg, 9, 71-79 (1995).

Lang et al., Circulation 75(1): 229-234 (Jan. 1987) Contrast Ultrasonography of the Kidney: a New Method for Evaluation of Renal Perfusion in Vivo*.

Lee et al.; "Arrays of Mulielement Ultrasound Applicators for Interstitial Hyperthermia"; *IEEE Transactions on biomedical Engineering*; vol. 46, No. 7; Jul. 1999.

Leong et al., Biomaterials, vol. 7: 364-371 (Sep. 1986) Polyanhydrides for Controlled Release of Bioactive Agents*.

Meltzer et al., J. Clin. Ultrasound 8(2): 121-7 (Apr. 1980) The Source of Ultrsound Contrast Effect*.

Miller, Douglas L. et al.; Sonoporation of Cultured Cells in the Rotation Tube Exposure System, vol. 25, No. 1, 1999.

Orkin and Motulsky, *Report and Recommendations of the Panel to Assess the NIH Investment in Research on Gene Therapy*, (p. 1-38, Dec. 7, 1995).

PCT Search Report, PCT Application PCT/US2006/13531; Apr. 12, 2006.

Porter, et al "Interaction of Diagnostic Ultrasound with Synthetic Olionucleotide-Labeled Perfluorcarbon-Exposed Sonicated Dextrose Albumin Microbubbles," J Ultrasound Med, 15:557-584, 1996.

Porter, T.R. et al., Thrombolytic Enhancement With Perfluorocarbom-Exposed Sonicated Dextrose Albumin Microbubbles, Nov. 1996.

Prat, F. et al.; In Vivo Effects of Cavitation Alone or in Combination Wity Chemotherapy in a Peritoneal Carinomatosis in the Rat. vol. 68, pp. 13-17.

Price, Richard et al.; Delivery of Colloidal Particles and Red Blood Cells to Tissue Through Microvessel Ruptures Created by Targeted Microbubble Destruction With Ultrasound, Sep. 29, 1998.

Romano et al., *Latest Developments in Gene Transfer Technology: Achievements, Perspectives, and Controversies over Therapeutice Applications*, (Stem Cells 18: 19-39, 2000).

Rosenschein, U. et al., Experimental Ultrasonic Angioplasty: Disruption of Atherosclerotic Plaques and Thrombi in Vitro and Arterial Recanalization in.

Somia and Verma, *Gene Therapy: Trials and Tribulations*, (Nature Reviews Genetics 1:91-99, 2000).

Tachibana K.; Albumin Microbubble Echo-Contrast Materials as an Enhancer for Ultrasound Accelerated Thrombolysis, Sep. 1, 1995.

Tachibana, K. "Enhancement of Fibrinolysis with Ultrasound Energy", JVIR, vol. 3, No. 2, May 1992, pp. 299-303.

Tsetis et al., "Potential Benefits From Heating the High-Dose Rtpa Boluses Used in Catheter-Directed Thrombolysis for Acute/Sub-acute Lower Limb Ischemia", J Endovasc. Ther. 10:739-744 (2003).

Tsurumi, et al. "Direct Intramuscular Gene Transfer of Naked DNA Encoding Vascular Endothelial Growth Factor Augments Collateral Development and Tissue Perfusion," Circulation, 1996; 94: 3281-3290.

Unger, et al. "Ultrasound Enhances Gene Expression of Liposomal Transfection," Investigative Radiology, vol. 32, No. 12, pp. 723-727, 1997.

Unger, Evan C. et al.; Acoustically Active Liposheres Containing Paclitaxel, vol. 11, No. 12, 1992.

Vandenburg et al., Am. Heart J., 115(4), 733-9 (Apr. 1988) Myocardial Risk Area and Peak Gray Level Measurement by Contrast Echocardiography: Effecct of Microbubble Size and Concentration, Injection Rate, and Coronary Vasodilation*.

Verma et al., *Gene Therapy—promises, problems and prospects*, (Nature 389: 239-242, 1997).

Wheatly et al., Biomaterials 11(19): 713-7 (Nov. 1990) Contrast Agents for Diagnostic Ultrsound: Development and Evaluation of Polymer-Coated Microbubbles*.

Wu, Yunqiu et al., Binding as Lysing of Blood Clots Using MRX-408, May 1998.

Wyber, et al. "The Use of Sonication for the Efficient Delivery of Plasmid DNA into Cells," Pharmaceutical Research, vol. 14, No. 6, pp. 750-756.

Gilles, et al. Cavitation Generated by Amplitude Modulated HIFU: Invetigation on the Inertial Cavitation Threshold, AIP Conference May 21, 2007, vol. 911, pp. 171-177.

Saletes, Izella, "Acoustic cavitation generated by bifrequency excitation" University De Lyon Dec. 2009.

Saletes, et al. Efficacite d'une Excitation Bifrequentielle en Thrombolyse Purement Ultrasonore Apr. 12-16, 2010.

Schafer, et al., "Influence of Ultrasound Opoerating Parameters on Ultrasound-Induced Thrombolysis in Vitro"; Ultrasound in Med. & Biol., vol. 31, No. 6, pp. 841-847, 2005.

* cited by examiner

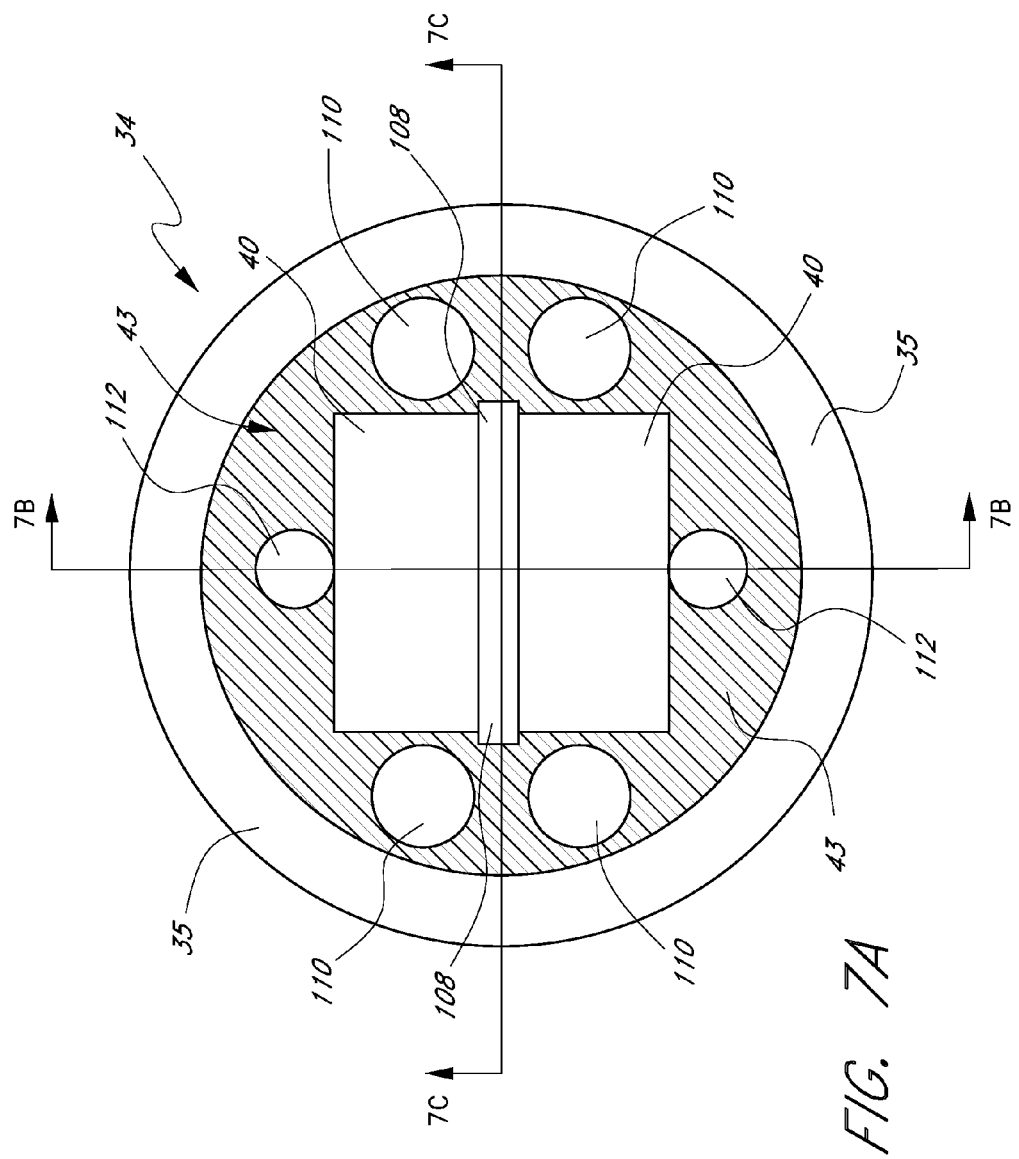

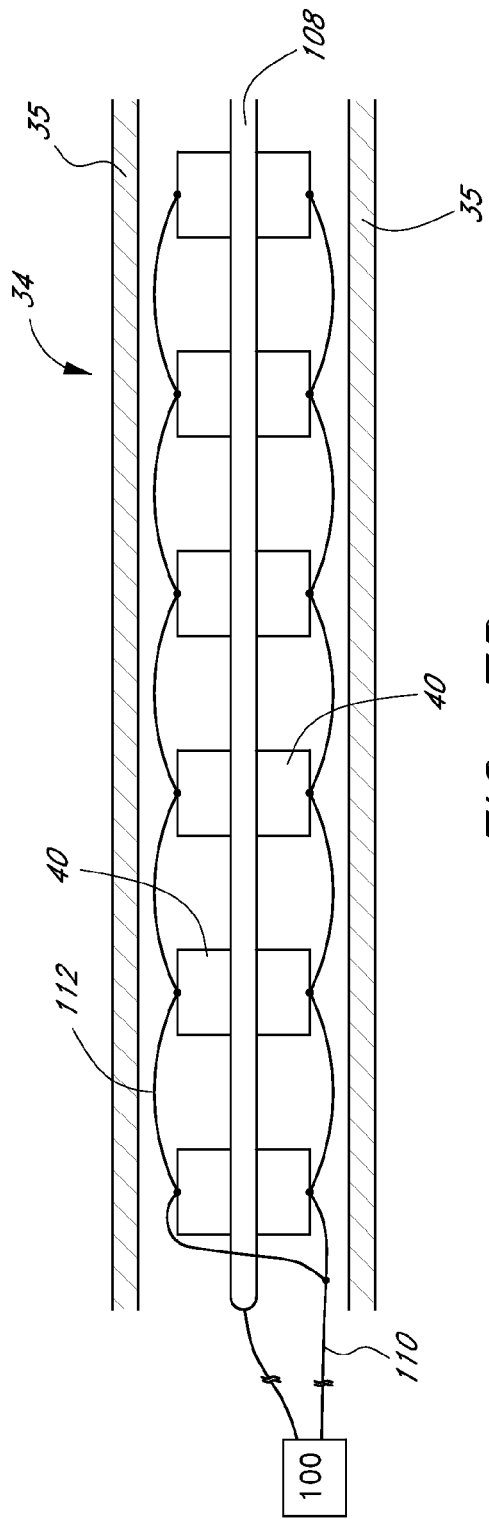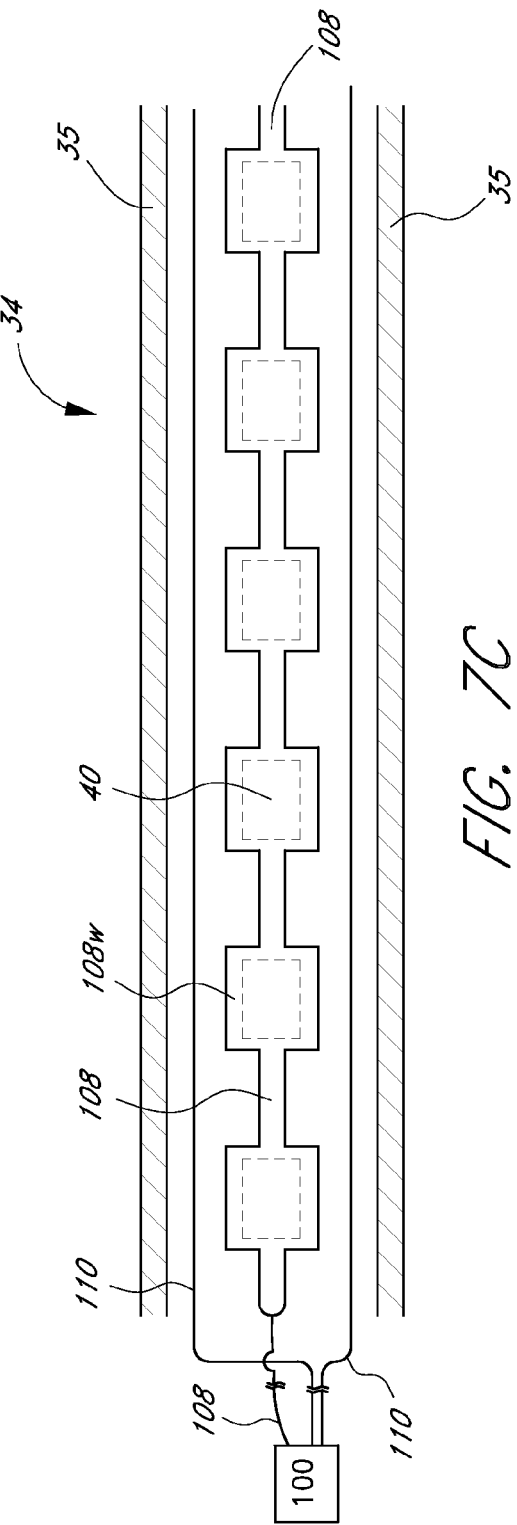

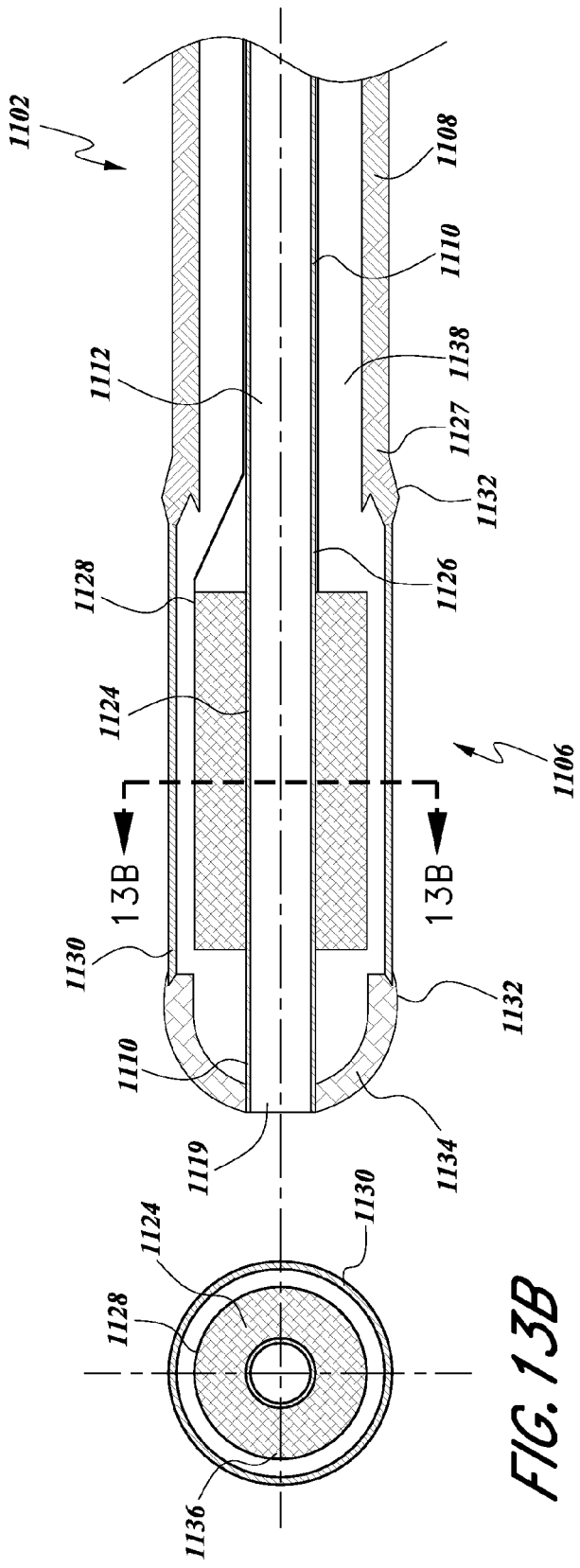

ated catheter positioned at the treatment site of FIG. 11A.
ULTRASONIC CATHETER POWER CONTROL

PRIORITY APPLICATION

This application is a divisional of U.S. application Ser. No. 10/405,423, filed Apr. 1, 2003; which claims the benefit of U.S. Provisional Application 60/369,438, filed 1 Apr. 2002.

FIELD OF THE INVENTION

The present invention relates generally to an ultrasonic catheter, and more specifically to an ultrasonic catheter configured to deliver ultrasonic energy and a therapeutic compound to a treatment site.

BACKGROUND OF THE INVENTION

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site in a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, such ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing dissolution compounds directly to the occlusion site. Ultrasonic energy generated by the ultrasound assembly enhances the therapeutic effect of the dissolution compounds. For example, in one application of such an ultrasonic catheter, an ultrasound-enhanced thrombolytic therapy dissolves blood clots in arteries and veins in the treatment of diseases such as peripheral arterial occlusion or deep vein thrombosis. In such applications, ultrasonic energy enhances thrombolysis with agents such as urokinase, tissue plasminogen activator ("TPA") and the like.

Ultrasonic catheters can also be used to enhance gene therapy at a treatment site within the patient's body. For example, U.S. Pat. No. 6,135,976 discloses an ultrasonic catheter having one or more expandable sections capable of occluding a section of a body lumen, such as a blood vessel. A gene therapy composition is then delivered to the occluded vessel through the catheter fluid delivery lumen. Ultrasonic energy generated by the ultrasound assembly is applied to the occluded vessel, thereby enhancing the delivery of a genetic composition into the cells of the occluded vessel.

Ultrasonic catheters can also be used to enhance delivery and activation of light activated drugs. For example, U.S. Pat. No. 6,176,842 discloses methods for using an ultrasonic catheter to treat biological tissues by delivering a light activated drug to the biological tissues and exposing the light activated drug to ultrasound energy.

The entire disclosure of all the patents listed in this "BACKGROUND OF THE INVENTION" section is hereby incorporated herein by reference in their entirety.

SUMMARY OF THE INVENTION

According to one embodiment of the present invention, method of treating an occlusion at a treatment site within a patient's vasculature comprises providing an ultrasonic catheter. The ultrasonic catheter has a distal region, a proximal region opposite the distal region, a fluid delivery lumen having at least one opening in the distal region, and an ultrasound radiating member positioned within the distal region. The method further comprises positioning the ultrasonic catheter at the treatment site, such that at least a portion of the distal region is within the occlusion. The ultrasonic catheter further comprises passing a therapeutic compound through the fluid delivery lumen such that the therapeutic compound is delivered to the treatment site. The ultrasonic catheter further comprises emitting ultrasonic energy from the ultrasound radiating member. The emitted ultrasonic energy has an amplitude that is periodically varied between a low amplitude and a high amplitude.

According to another embodiment of the present invention, a method comprises providing a catheter having a plurality of ultrasound radiating members. The plurality of ultrasound radiating members are allocated into electrical groups comprising more than one ultrasound radiating member. The method further comprises delivering a therapeutic compound through the catheter to a treatment site within a patient's vasculature. The method further comprises independently driving each group of ultrasound radiating members. The ultrasound radiating members are configured to periodically deliver pulses of ultrasonic energy to the treatment site, wherein the pulses of ultrasonic energy having a pulse duration.

BRIEF DESCRIPTION OF THE DRAWINGS

FIG. 7A is a schematic illustration of the ultrasound assembly of FIG. 5 housed within the inner core of FIG. 4.

FIG. 7B is a cross-sectional view of the ultrasound assembly of FIG. 7A taken along line 7B-7B.

FIG. 7C is a cross-sectional view of the ultrasound assembly of FIG. 7A taken along line 7C-7C.

FIG. 13A is a cross-sectional view of a distal end of the ultrasound catheter of FIG. 12.

FIG. 13B is a cross-sectional view of the ultrasound catheter taken through line 13B-13B of FIG. 13A.

DETAILED DESCRIPTION OF PREFERRED EMBODIMENTS

Figure 1:
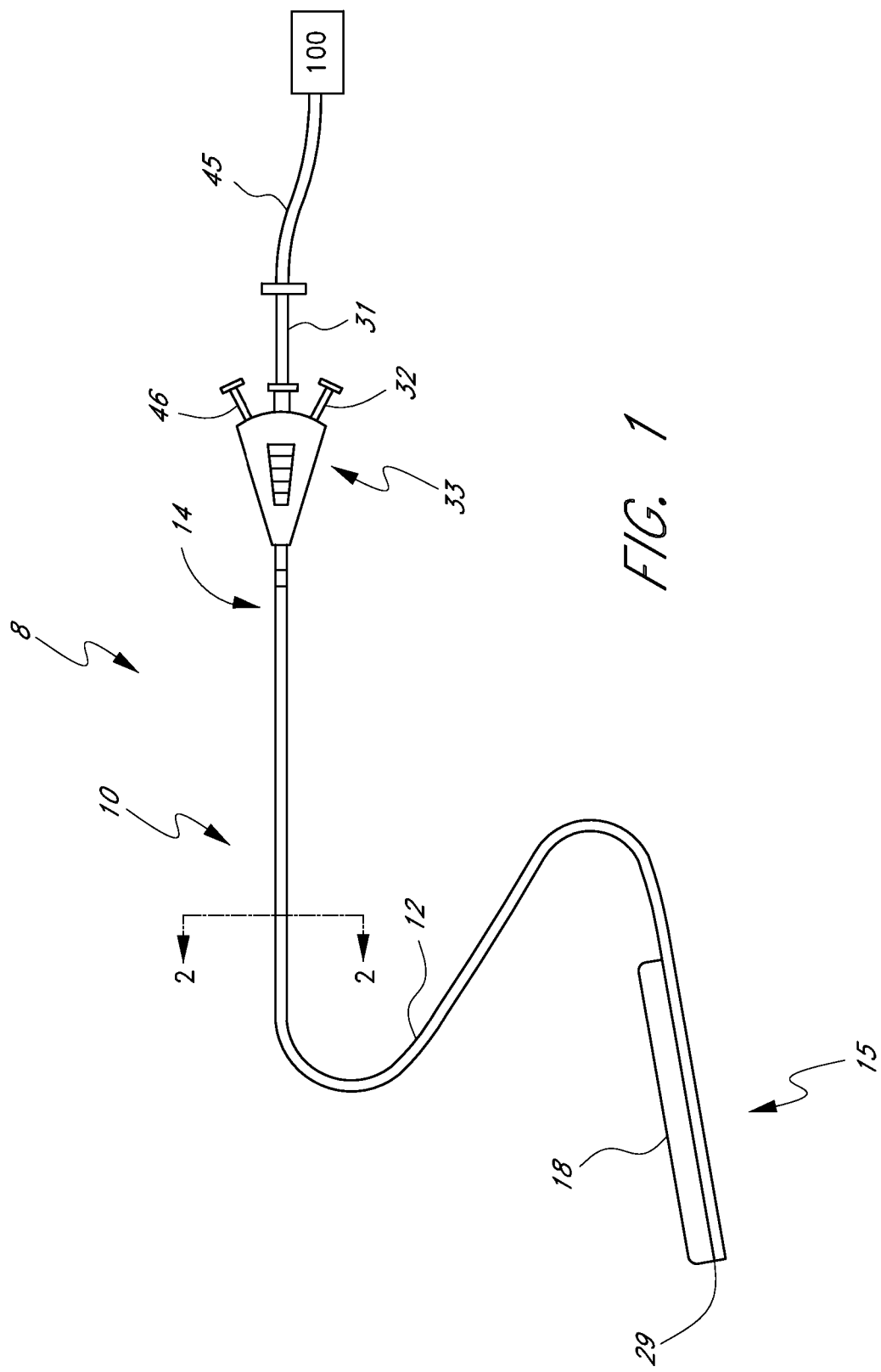
FIG. 1 is a schematic illustration of an ultrasonic catheter configured for insertion into large vessels of the human body.

As described above, it is desired to provide an ultrasonic catheter having various features and advantages. Examples of such features and advantages include the ability to deliver multi-frequency ultrasonic energy to a treatment site within a patient's vasculature. Preferred embodiments of an ultrasonic catheter having certain of these features and advantages are described herein. Methods of using such an ultrasonic catheter are also described herein.

The ultrasonic catheters described herein can be used to enhance the therapeutic effects of therapeutic compounds at a treatment site within a patient's body. As used herein, the term "therapeutic compound" refers broadly, without limitation, to a drug, medicament, dissolution compound, genetic material or any other substance capable of effecting physiological functions. Additionally, any mixture comprising any such substances is encompassed within this definition of "therapeutic compound", as well as any substance falling within the ordinary meaning of these terms. The enhancement of the effects of therapeutic compounds using ultrasonic energy is described in U.S. Pat. Nos. 5,318,014, 5,362,309, 5,474,531, 5,628,728, 6,001,069, 6,096,000, 6,210,356 and 6,296,619, the entire disclosure of which is hereby incorporated by herein by reference. Specifically, for applications that treat human blood vessels that have become partially or completely occluded by plaque, thrombi, emboli or other substances that reduce the blood carrying capacity of a vessel, suitable therapeutic compounds include, but are not limited to, an aqueous solution containing Heparin, Uronkinase, Streptokinase, TPA and BB-10153 (manufactured by British Biotech, Oxford, UK).

Certain features and aspects of the ultrasonic catheters disclosed herein may also find utility in applications where the ultrasonic energy itself provides a therapeutic effect. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,269,291 and 5,431,663, the entire disclosure of which is hereby incorporated herein by reference. Further information about using cavitation to produce biological effects can be found in U.S. Pat. No. RE36,939, the entire disclosure of which is hereby incorporated herein by reference.

The ultrasonic catheters described herein are configured for applying ultrasonic energy over a substantial length of a body lumen, such as, for example, the larger vessels located in the leg. However, it should be appreciated that certain features and aspects of the present invention may be applied to catheters configured to be inserted into the small cerebral vessels, in solid tissues, in duct systems and in body cavities. Such catheters are described in U.S. patent application Ser. No. 10/309,417, entitled "Small Vessel Ultrasound Catheter" and filed Dec. 3, 2002, the entire disclosure of which is hereby incorporated herein by reference. Additional embodiments that may be combined with certain features and aspects of the embodiments described herein are described in U.S. patent application Ser. No. 10/291,891, entitled "Ultrasound Assembly For Use With A Catheter" and filed Nov. 7, 2002, the entire disclosure of which is hereby incorporated herein by reference.

For purposes of summarizing the invention and the advantages achieved over the prior art, certain objects and advantages of the invention have been described above. It is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment or embodiments disclosed.

Overview of a Large Vessel Ultrasound Catheter

With initial reference to FIG. 1, an ultrasonic catheter 10 configured for use in the large vessels of a patient's anatomy is schematically illustrated. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally comprises a multi-component, elongate flexible tubular body 12 having a proximal region 14 and a distal region 15. The tubular body 12 includes a flexible energy delivery section 18 and a distal exit port 29 located in the distal region 15 of the catheter 10. A backend hub 33 is attached to the proximal region 14 of the tubular body 12, the backend hub 33 comprising a proximal access port 31, an inlet port 32 and a cooling fluid fitting 46. The proximal access port 31 can be connected to control circuitry 100 via cable 45.

The tubular body 12 and other components of the catheter 10 can be manufactured in accordance with any of a variety of techniques well known in the catheter manufacturing field. Suitable materials and dimensions can be readily selected based on the natural and anatomical dimensions of the treatment site and on the desired percutaneous access site.

For example, in a preferred embodiment the proximal region 14 of the tubular body 12 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the proximal region 14 of the tubular body 12 is reinforced by braiding, mesh or other constructions to provide increased kink resistance and pushability. For example, nickel titanium or stainless steel wires can be placed along or incorporated into the tubular body 12 to reduce kinking.

In an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths may by appropriate for other applications.

The energy delivery section 18 of the tubular body 12 preferably comprises a material that is thinner than the material comprising the proximal region 14 of the tubular body 12 or a material that has a greater acoustic transparency. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 may be formed from the same material or a material of the same thickness as the proximal region 14.

In certain embodiments, the tubular body 12 is divided into at least three sections of varying stiffness. The first section, which preferably includes the proximal region 14, has a relatively higher stiffness. The second section, which is located in an intermediate region between the proximal region 14 and the distal region 15 of the tubular body 12, has a relatively lower stiffness. This configuration further facilitates movement and placement of the catheter 10. The third section, which preferably includes the energy delivery section 18, generally has a lower stiffness than the second section.

Figure 2:
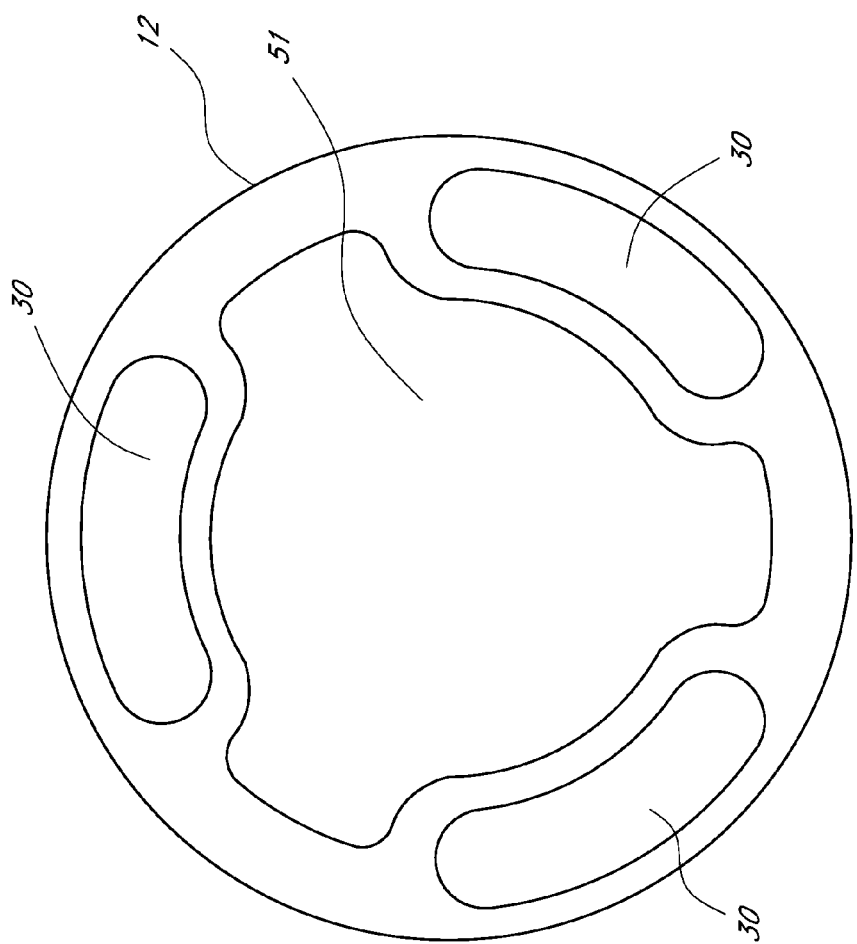
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. The arrangement of the fluid delivery lumens 30 preferably provides a hollow central lumen 51 passing through the tubular body 12. The cross-section of the tubular body 12, as illustrated in FIG. 2, is preferably substantially constant along the length of the catheter 10. Thus, in such embodiments, substantially the same cross-section is present in both the proximal region 14 and the distal region 15 of the catheter 10, including the energy delivery section 18.

In certain embodiments, the central lumen 51 has a minimum diameter greater than about 0.030 inches. In another embodiment, the central lumen 51 has a minimum diameter greater than about 0.037 inches. In one preferred embodiment, the fluid delivery lumens 30 have dimensions of about 0.026 inches wide by about 0.0075 inches high, although other dimensions may be used in other applications.

As described above, the central lumen 51 preferably extends through the length of the tubular body 12. As illustrated in FIG. 1, the central lumen 51 preferably has a distal exit port 29 and a proximal access port 31. The proximal access port 31 forms part of the backend hub 33, which is attached to the proximal region 14 of the catheter 10. The backend hub 33 preferably further comprises cooling fluid fitting 46, which is hydraulically connected to the central lumen 51. The backend hub 33 also preferably comprises a therapeutic compound inlet port 32, which is in hydraulic connection with the fluid delivery lumens 30, and which can be hydraulically coupled to a source of therapeutic compound via a hub such as a Luer fitting.

Figure 3:
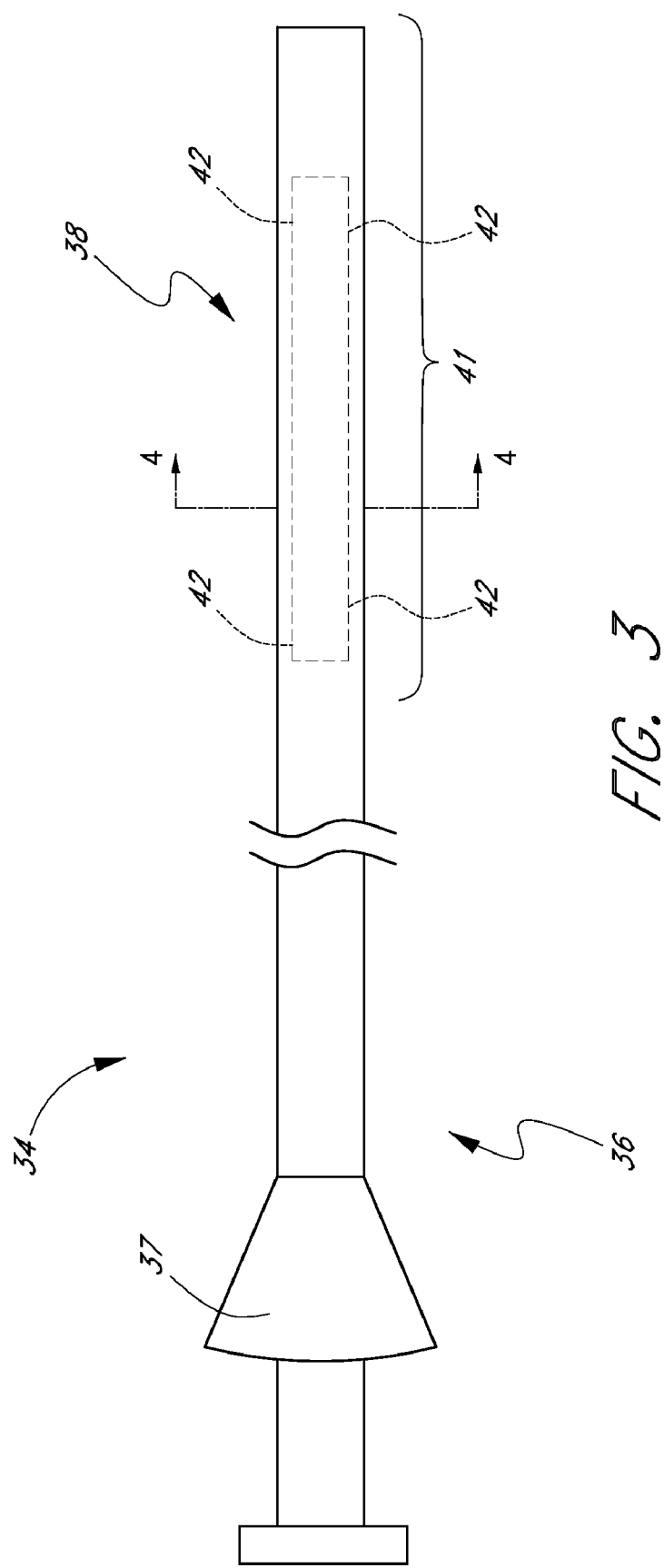
FIG. 3 is a schematic illustration of an elongate inner core configured to be positioned within the central lumen of the catheter illustrated in FIG. 2.

The central lumen 51 is configured to receive an elongate inner core 34 of which a preferred embodiment is illustrated in FIG. 3. The elongate inner core 34 preferably comprises a proximal region 36 and a distal region 38. Proximal hub 37 is fitted on the inner core 34 at one end of the proximal region 36. One or more ultrasound radiating members are positioned within an inner core energy delivery section 41 located within the distal region 38. The ultrasound radiating members form an ultrasound assembly 42, which will be described in greater detail below.

Figure 4:
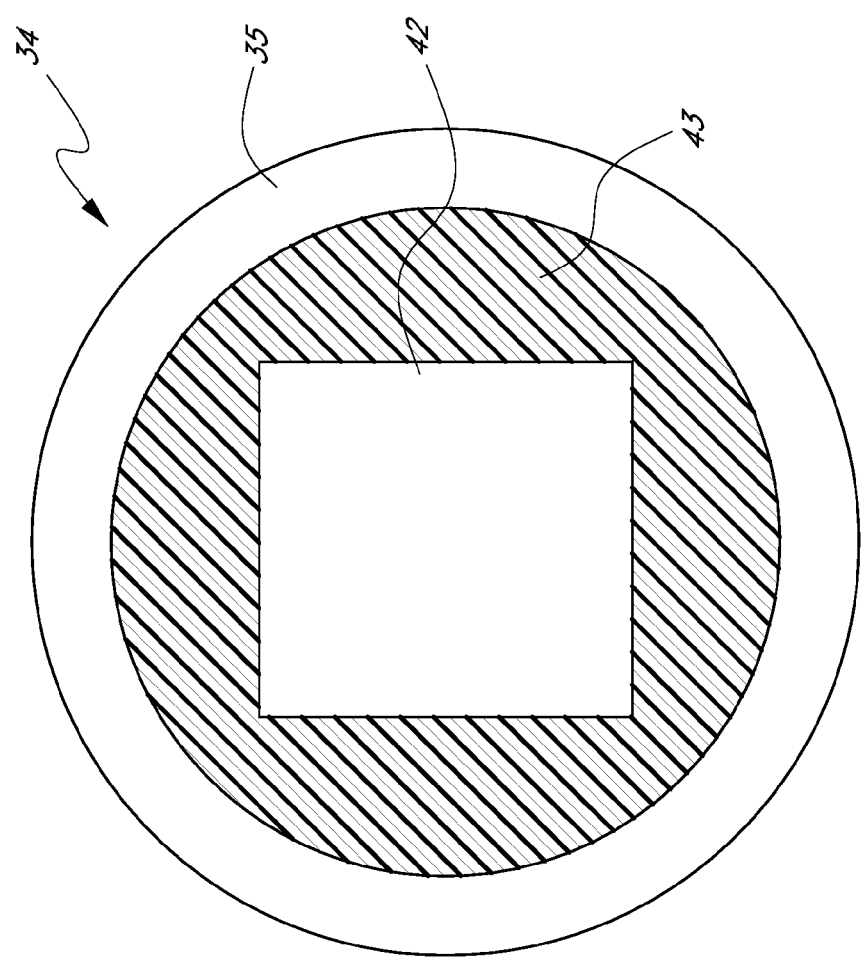
FIG. 4 is a cross-sectional view of the elongate inner core of FIG. 3 taken along line 4-4.

As shown in the cross-section illustrated in FIG. 4, which is taken along lines 4-4 in FIG. 3, the inner core 34 preferably has a cylindrical shape, with an outer diameter that permits the inner core 34 to be inserted into the central lumen 51 of the tubular body 12 via the proximal access port 31. Suitable outer diameters of the inner core 34 include, but are not limited to, about 0.010 inches to about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 preferably comprises a cylindrical outer body 35 that houses the ultrasound assembly 42. The ultrasound assembly 42 comprises wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to control circuitry 100 via cable 45 (illustrated in FIG. 1). Preferably, an electrically insulating potting material 43 fills the inner core 34, surrounding the ultrasound assembly 42, thus preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
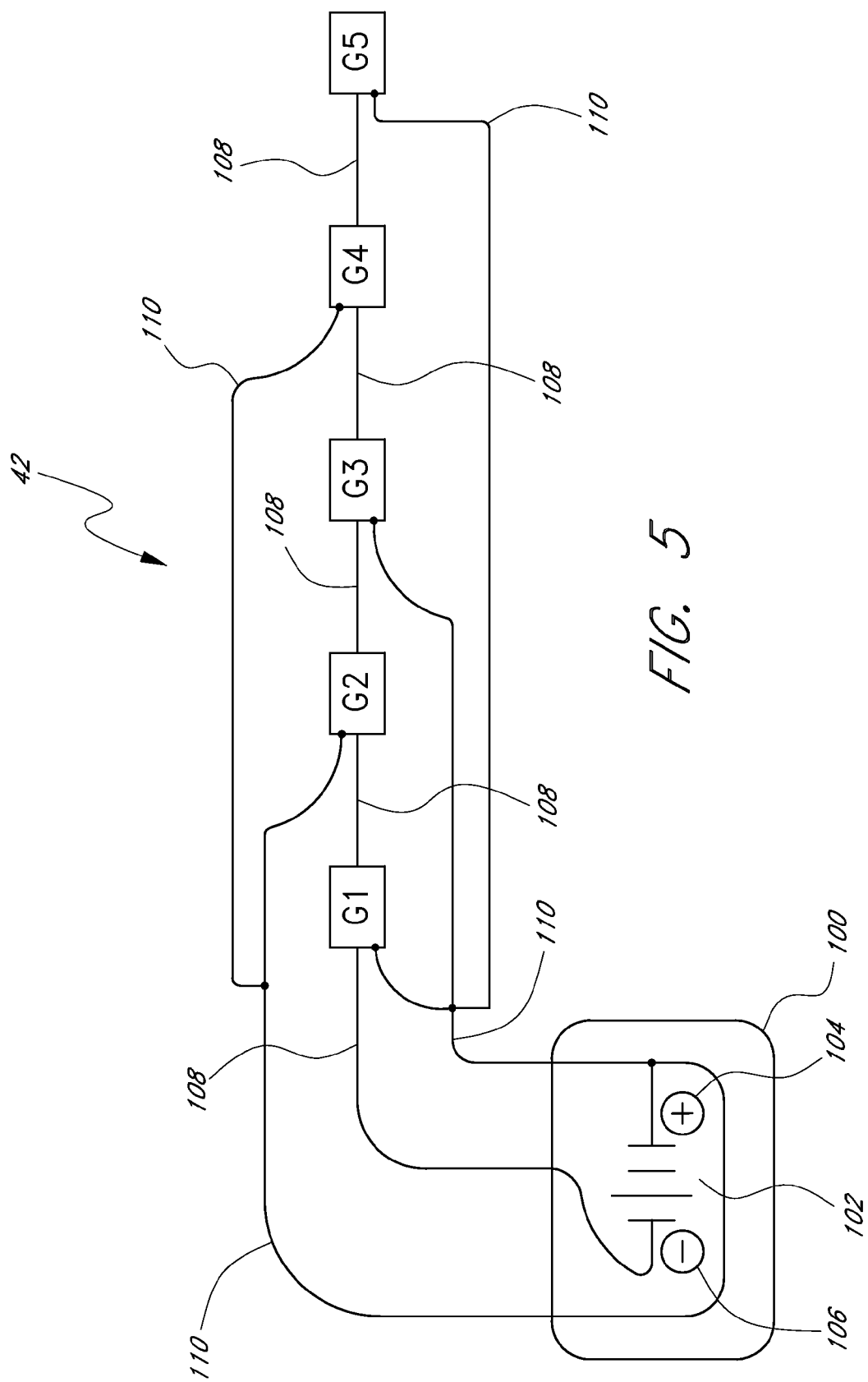
FIG. 5 is a schematic wiring diagram illustrating a preferred technique for electrically connecting five groups of ultrasound radiating members to form an ultrasound assembly.
Figure 6:
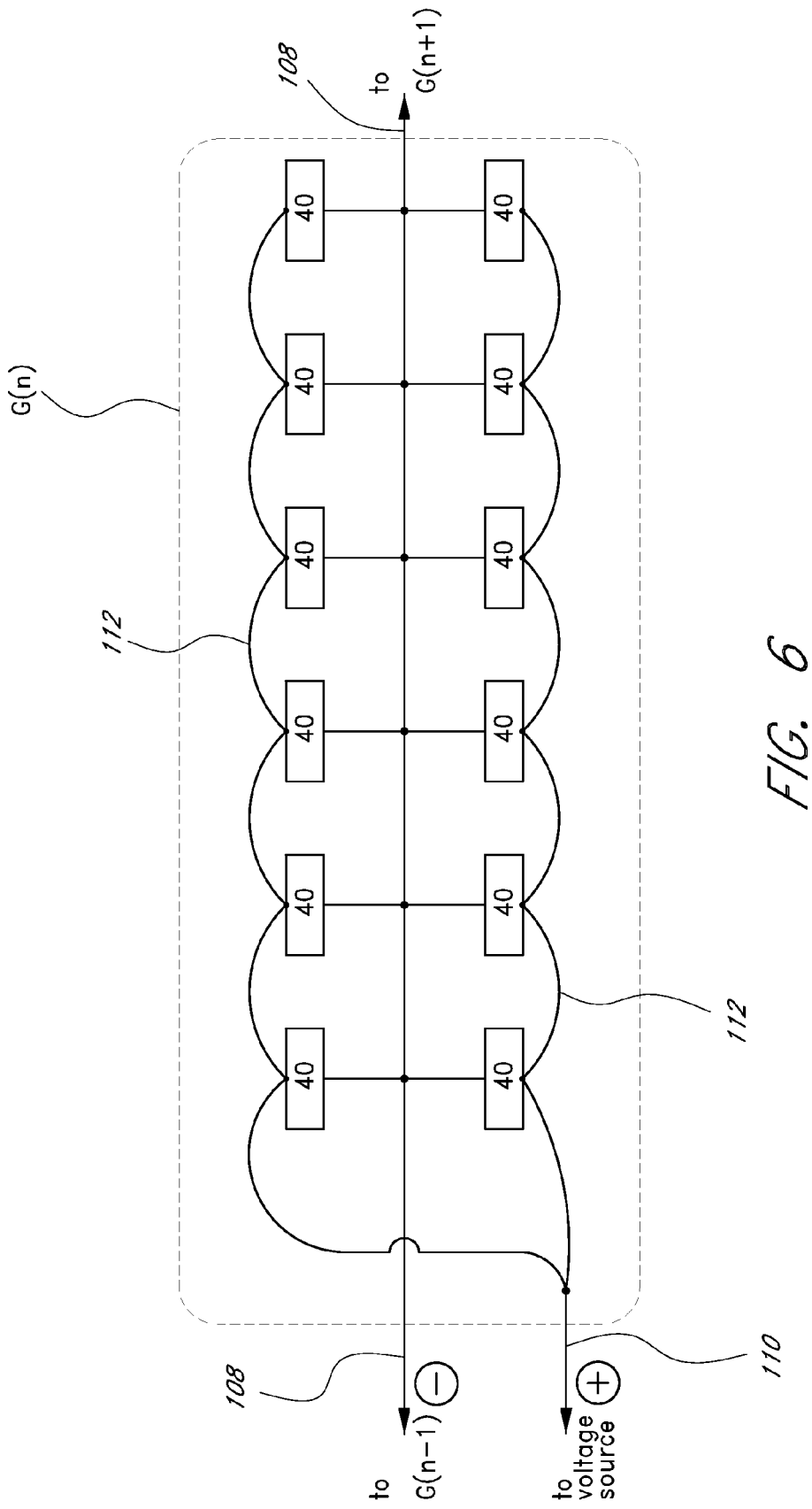
FIG. 6 is a schematic wiring diagram illustrating a preferred technique for electrically connecting one of the groups of FIG. 5.

In a preferred embodiment, the ultrasound assembly 42 comprises a plurality of ultrasound radiating members that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control circuitry 100.

As used herein, the terms "ultrasonic energy", "ultrasound" and "ultrasonic" are broad terms, having their ordinary meanings, and further refer to, without limitation, mechanical energy transferred through longitudinal pressure or compression waves. Ultrasonic energy can be emitted as continuous or pulsed waves, depending on the requirements of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy has a frequency between about 20 kHz and about 20 MHz. For example, in one embodiment, the waves have a frequency between about 500 kHz and about 20 MHz. In another embodiment, the waves have a frequency between about 1 MHz and about 3 MHz. In yet another embodiment, the waves have a frequency of about 2 MHz. The average acoustic power is between about 0.01 watts and 300 watts. In one embodiment, the average acoustic power is about 15 watts.

As used herein, the term "ultrasound radiating member" refers to any apparatus capable of producing ultrasonic energy. For example, in one embodiment, an ultrasound radiating member comprises an ultrasonic transducer, which converts electrical energy into ultrasonic energy. A suitable example of an ultrasonic transducer for generating ultrasonic energy from electrical energy includes, but is not limited to, piezoelectric ceramic oscillators. Piezoelectric ceramics typically comprise a ceramic material, such as lead zirconate titanate ("PZT"), that change shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

Still referring to FIG. 5, the control circuitry 100 preferably comprises, among other things, a voltage source 102. The voltage source 102 comprises a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 comprises a plurality of ultrasound radiating members 40. Each of the ultrasound radiating members 40 is electrically connected to the common wire 108 and to the lead wire 110 via one of two positive contact wires 112. Thus, when wired as illustrated, a constant voltage difference will be applied to each ultrasound radiating member 40 in the group. Although the group illustrated in FIG. 6 comprises twelve ultrasound radiating members 40, one of ordinary skill in the art will recognize that more or fewer ultrasound radiating members 40 can be included in the group. Likewise, more or fewer than five groups can be included within the ultrasound assembly 42 illustrated in FIG. 5.

FIG. 7A illustrates one preferred technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

Referring still to FIG. 7A, the common wire 108 comprises an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. Lead wires 110 are preferably separated from the other components of the ultrasound assembly 42, thus preventing interference with the operation of the ultrasound radiating members 40 as described above. For example, in one preferred embodiment, the inner core 34 is filled with an insulating potting material 43, thus deterring unwanted electrical contact between the various components of the ultrasound assembly 42.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 preferably comprises wide regions 108W upon which the ultrasound radiating members 40 can be mounted, thus reducing the likelihood that the paired ultrasound radiating members 40 will short together. In certain embodiments, outside the wide regions 108W, the common wire 108 may have a more conventional, rounded wire shape.

Figure 7D:
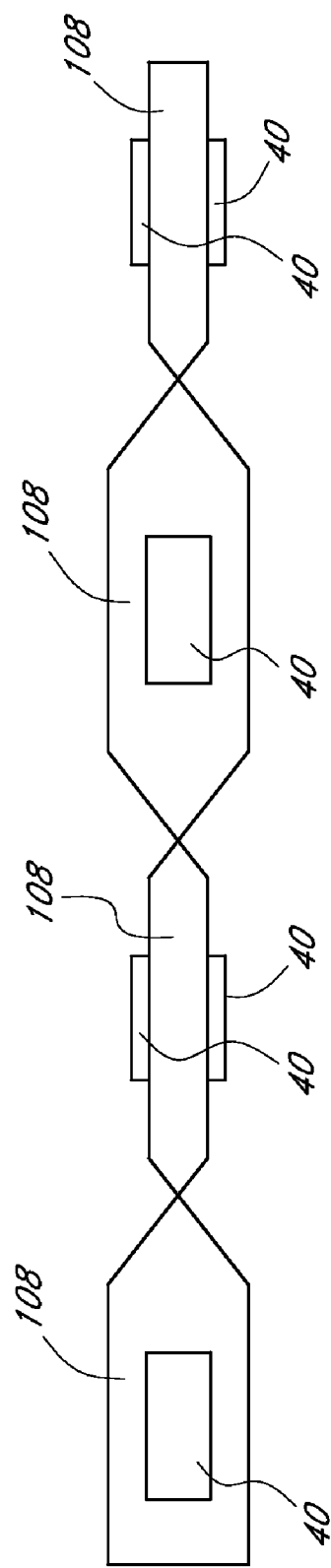
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

One of ordinary skill in the art will recognize that the wiring arrangement described above can be modified to allow each group G1, G2, G3, G4, G5 to be independently powered. Specifically, by providing a separate power source within the control system 100 for each group, each group can be individually turned on or off, or can be driven with an individualized power. This provides the advantage of allowing the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, illustrate a plurality of ultrasound radiating members grouped spatially. That is, in such embodiments, all of the ultrasound radiating members within a certain group are positioned adjacent to each other, such that when a single group is activated, ultrasonic energy is delivered at a specific length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the energy delivery section. Such modified embodiments may be advantageous in applications wherein it is desired to deliver a less focussed, more diffuse ultrasonic energy field to the treatment site.

In a preferred embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations may be used. For example, disc-shaped ultrasound radiating members 40 can be used in other embodiments. In a preferred embodiment, the common wire 108 comprises copper, and is about 0.005 inches thick, although other electrically conductive materials and other dimensions can be used in other embodiments. Lead wires 110 are preferably 36-gauge electrical conductors, while positive contact wires 112 are preferably 42-gauge electrical conductors. However, one of ordinary skill in the art will recognize that other wire gauges can be used in other embodiments.

As described above, suitable frequencies for the ultrasound radiating member 40 include, but are not limited to, from about 20 kHz to about 20 MHz. In one embodiment, the frequency is between about 500 kHz and 20 MHz, and in another embodiment the frequency is between about 1 MHz and 3 MHz. In yet another embodiment, the ultrasound radiating members 40 are operated with a frequency of about 2 MHz.

Figure 8:
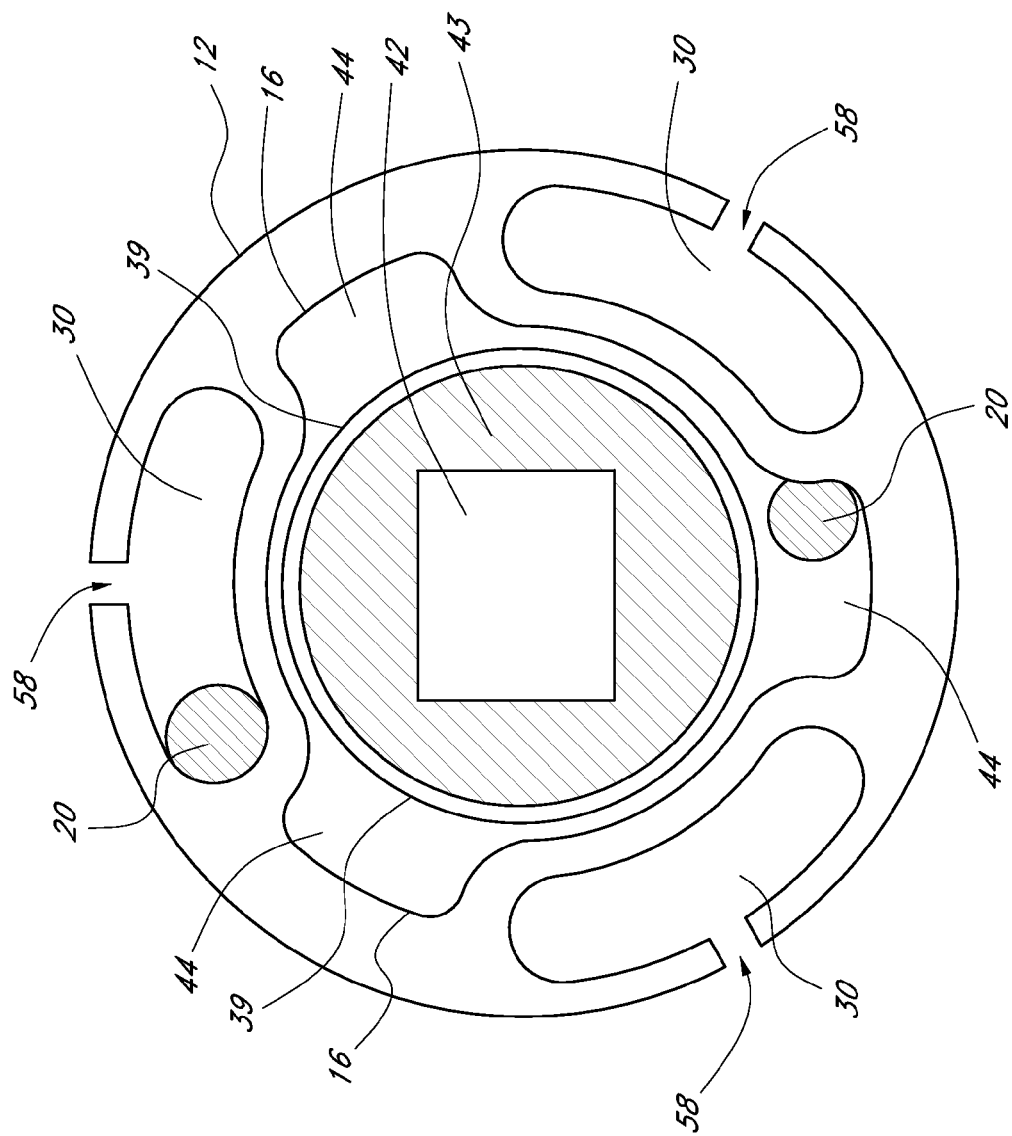
FIG. 8 illustrates the energy delivery section of the inner core of FIG. 4 positioned within the energy delivery section of the tubular body of FIG. 2.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in a preferred embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. Thus, a source of therapeutic compound coupled to the inlet port 32 provides a hydraulic pressure which drives the therapeutic compound through the fluid delivery lumens 30 and out the fluid delivery ports 58.

By evenly spacing the fluid delivery lumens 30 around the circumference of the tubular body 12, as illustrated in FIG. 8, a substantially even flow of therapeutic compound around the circumference of the tubular body 12 can be achieved. In addition, the size, location and geometry of the fluid delivery ports 58 can be selected to provide uniform fluid flow from the fluid delivery lumen 30 to the treatment site. For example, in one embodiment, fluid delivery ports 58 closer to the proximal region of the energy delivery section 18 have smaller diameters than fluid delivery ports 58 closer to the distal region of the energy delivery section 18, thereby allowing uniform delivery of fluid across the entire energy delivery section 18.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to 0.0020 inches in the distal region of the energy delivery section 18. The increase in size between adjacent fluid delivery ports 58 depends on the material comprising the tubular body 12, and on the size of the fluid delivery lumen 30. The fluid delivery ports 58 can be created in the tubular body 12 by punching, drilling, burning or ablating (such as with a laser), or by any other suitable method. Therapeutic compound flow along the length of the tubular body 12 can also be increased by increasing the density of the fluid delivery ports 58 toward the distal region 15 of the tubular body 12.

It should be appreciated that it may be desirable to provide non-uniform fluid flow from the fluid delivery ports 58 to the treatment site. In such embodiment, the size, location and geometry of the fluid delivery ports 58 can be selected to provide such non-uniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flow is produced through cooling fluid lumens 44 and out distal exit port 29 (see FIG. 1). The cooling fluid lumens 44 are preferably evenly spaced around the circumference of the tubular body 12 (that is, at approximately 120° increments for a three-lumen configuration), thereby providing uniform cooling fluid flow over the inner core 34. Such a configuration is desired to remove unwanted thermal energy at the treatment site. As will be explained below, the flow rate of the cooling fluid and the power to the ultrasound assembly 42 can be adjusted to maintain the temperature of the inner core energy delivery section 41 within a desired range.

In a preferred embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, the inner core outer body 35 preferably comprises a material having the ability to transmit torque. Suitable materials for the inner core outer body 35 include, but are not limited to, polyimides, polyesters, polyurethanes, thermoplastic elastomers and braided polyimides.

In a preferred embodiment, the fluid delivery lumens 30 and the cooling fluid lumens 44 are open at the distal end of the tubular body 12, thereby allowing the therapeutic compound and the cooling fluid to pass into the patient's vasculature at the distal exit port. Or, if desired, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can prevented from passing through the distal exit port by configuring the inner core 34 to have a length that is less than the length of the tubular body 12. In other embodiments, a protrusion is formed on the inner surface 16 of the tubular body 12 in the distal region 15, thereby preventing the inner core 34 from passing through the distal exit port 29.

In still other embodiments, the catheter 10 further comprises an occlusion device (not shown) positioned at the distal exit port 29. The occlusion device preferably has a reduced inner diameter that can accommodate a guidewire, but that is less than the outer diameter of the central lumen 51. Thus, the inner core 34 is prevented from extending through the occlusion device and out the distal exit port 29. For example, suitable inner diameters for the occlusion device include, but are not limited to, about 0.005 inches to about 0.050 inches. In other embodiments, the occlusion device has a closed end, thus preventing cooling fluid from leaving the catheter 10, and instead recirculating to the proximal region 14 of the tubular body 12. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In certain embodiments, as illustrated in FIG. 8, the tubular body 12 further comprises one or more temperature sensors 20, which are preferably located within the energy delivery section 18. In such embodiments, the proximal region 14 of the tubular body 12 includes a temperature sensor lead wire (not shown) which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermochromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
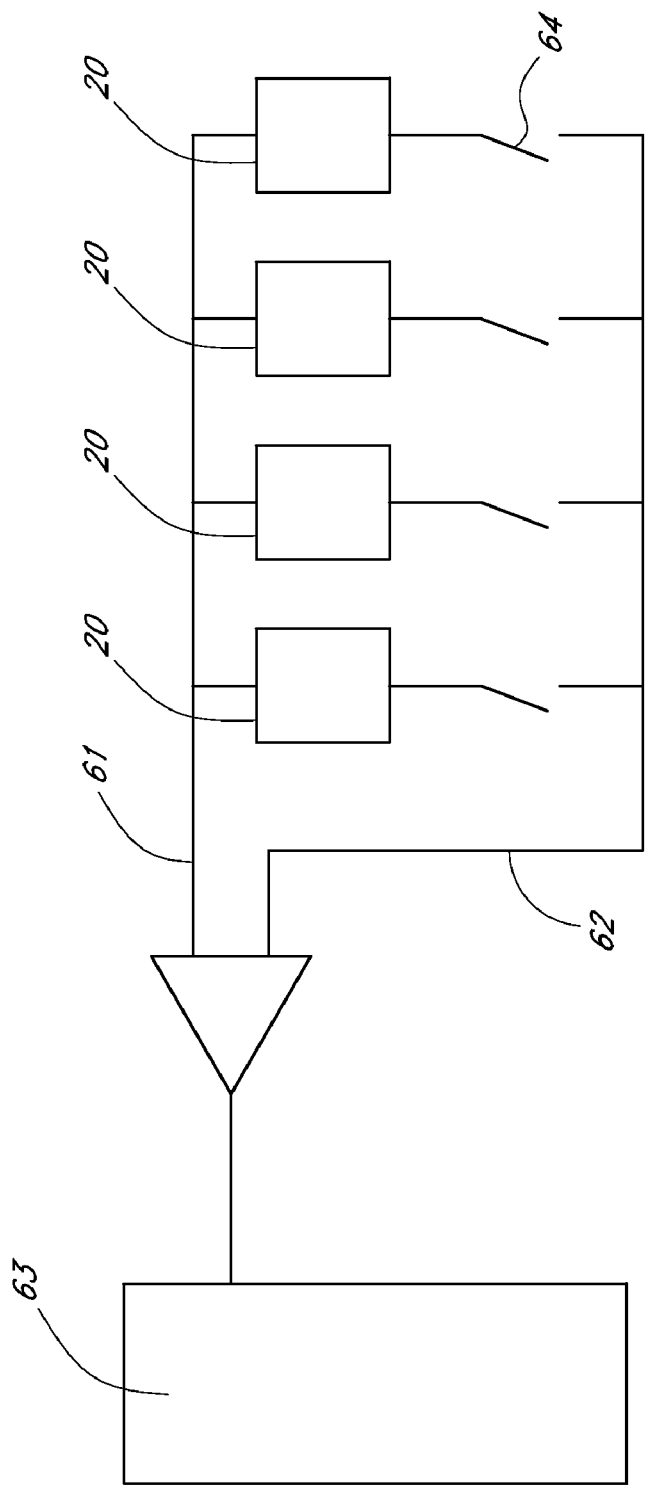
FIG. 9 illustrates a wiring diagram for connecting a plurality of temperature sensors with a common wire.

FIG. 9 illustrates one embodiment for electrically connecting the temperature sensors 20. In such embodiments, each temperature sensor 20 is coupled to a common wire 61 and is associated with an individual return wire 62. Accordingly, n+1 wires can be used to independently sense the temperature at n distinct temperature sensors 20. The temperature at a particular temperature sensor 20 can be determined by closing a switch 64 to complete a circuit between that thermocouple's individual return wire 62 and the common wire 61. In embodiments wherein the temperature sensors 20 comprise thermocouples, the temperature can be calculated from the voltage in the circuit using, for example, a sensing circuit 63, which can be located within the external control circuitry 100.

In other embodiments, each temperature sensor 20 is independently wired. In such embodiments, 2n wires pass through the tubular body 12 to independently sense the temperature at n independent temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
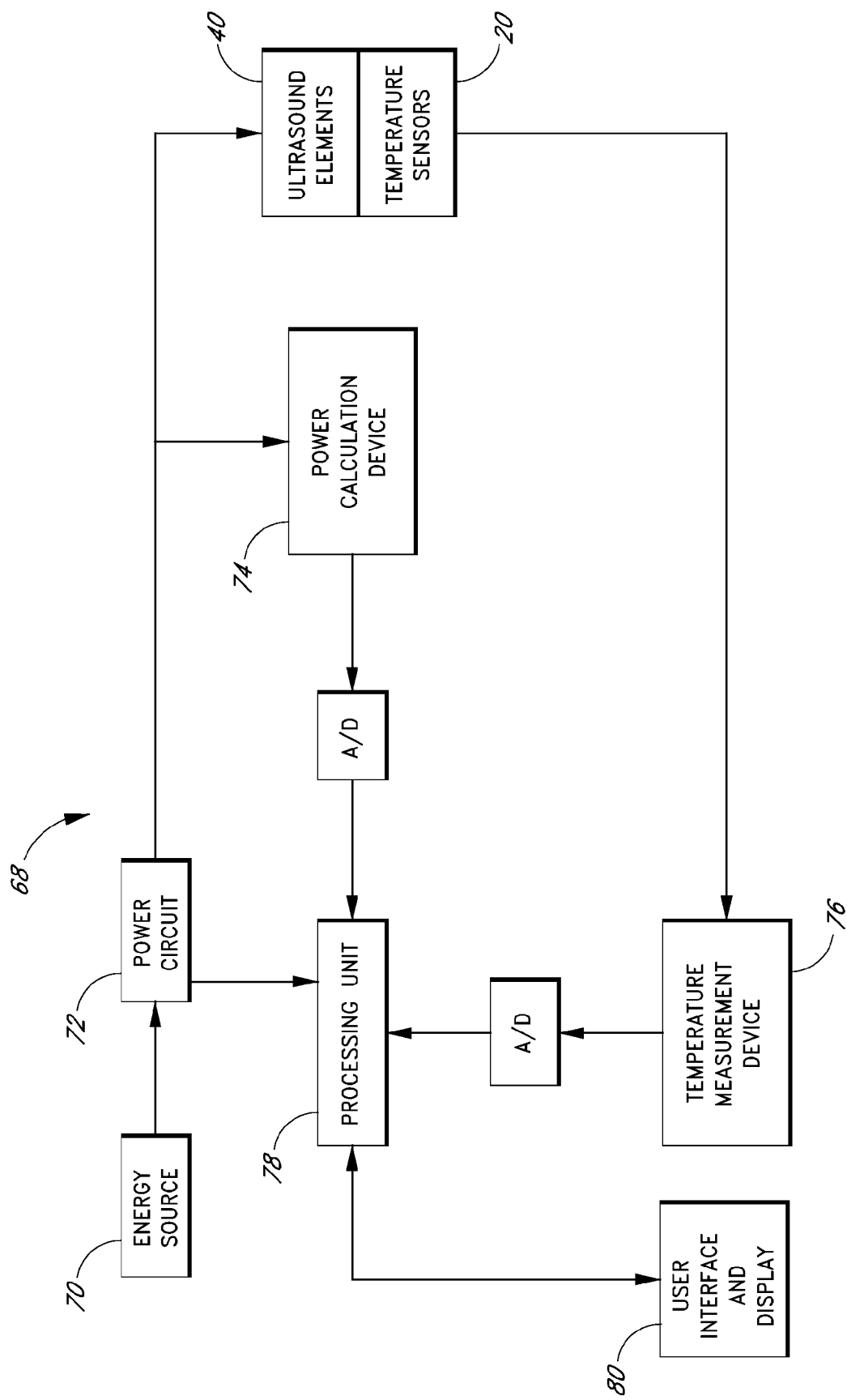
FIG. 10 is a block diagram of a feedback control system for use with an ultrasonic catheter.

FIG. 10 illustrates one embodiment of a feedback control system 68 that can be used with the catheter 10. The feedback control system 68 can be integrated into the control system that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

The feedback control system 68 preferably comprises an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In operation, the temperature at each temperature sensor 20 is determined by the temperature measurement device 76. The processing unit 78 receives each determined temperature from the temperature measurement device 76. The determined temperature can then be displayed to the user at the user interface and display 80.

The processing unit 78 comprises logic for generating a temperature control signal. The temperature control signal is proportional to the difference between the measured temperature and a desired temperature. The desired temperature can be determined by the user (set at the user interface and display 80) or can be preset within the processing unit 78.

The temperature control signal is received by the power circuits 72. The power circuits 72 are preferably configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is preferably reduced in response to that temperature control signal. Similarly, when the temperature control signal is below a particular level, the power supplied to a particular group of ultrasound radiating members 40 is preferably increased in response to that temperature control signal. After each power adjustment, the processing unit 78 preferably monitors the temperature sensors 20 and produces another temperature control signal which is received by the power circuits 72.

The processing unit 78 preferably further comprises safety control logic. The safety control logic detects when the temperature at a temperature sensor 20 has exceeded a safety threshold. The processing unit 78 can then provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating member 40 can be identically adjusted in certain embodiments. In a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 also receives a power signal from a power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, it is generally desirable to prevent tissue at a treatment site from increasing more than 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as for example a computer with software. When the processing unit 78 is a computer it can include a central processing unit ("CPU") coupled through a system bus. As is well known in the art, the user interface and display 80 can comprise a mouse, a keyboard, a disk drive, a display monitor, a nonvolatile memory system, or any another. Also preferably coupled to the bus is a program memory and a data memory.

In lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 can then be adjusted according to the preset profiles.

The ultrasound radiating members 40 are preferably operated in a pulsed mode. For example, in one embodiment, the time average power supplied to the ultrasound radiating members 40 is preferably between about 0.1 watts and 2 watts and more preferably between about 0.5 watts and 1.5 watts. In certain preferred embodiments, the time average power is approximately 0.6 watts or 1.2 watts. The duty cycle is preferably between about 1% and 50% and more preferably between about 5% and 25%. In certain preferred embodiments, the duty ratio is approximately 7.5% or 15%. The pulse averaged power is preferably between about 0.1 watts and 20 watts and more preferably between approximately 5 watts and 20 watts. In certain preferred embodiments, the pulse averaged power is approximately 8 watts and 16 watts. The amplitude during each pulse can be constant or varied.

In one embodiment, the pulse repetition rate is preferably between about 5 Hz and 150 Hz and more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

In one particular embodiment, the ultrasound radiating members 40 are operated at an average power of approximately 0.6 watts, a duty cycle of approximately 7.5%, a pulse repetition rate of 30 Hz, a pulse average electrical power of approximately 8 watts and a pulse duration of approximately 2.5 milliseconds.

The ultrasound radiating members 40 used with the electrical parameters described herein preferably has an acoustic efficiency greater than 50% and more preferably greater than 75%. The ultrasound radiating members 40 can be formed a variety of shapes, such as, cylindrical (solid or hollow), flat, bar, triangular, and the like. The length of the ultrasound radiating members 40 is preferably between about 0.1 cm and about 0.5 cm. The thickness or diameter of the ultrasound radiating members 40 is preferably between about 0.02 cm and about 0.2 cm.

Figure 11A:
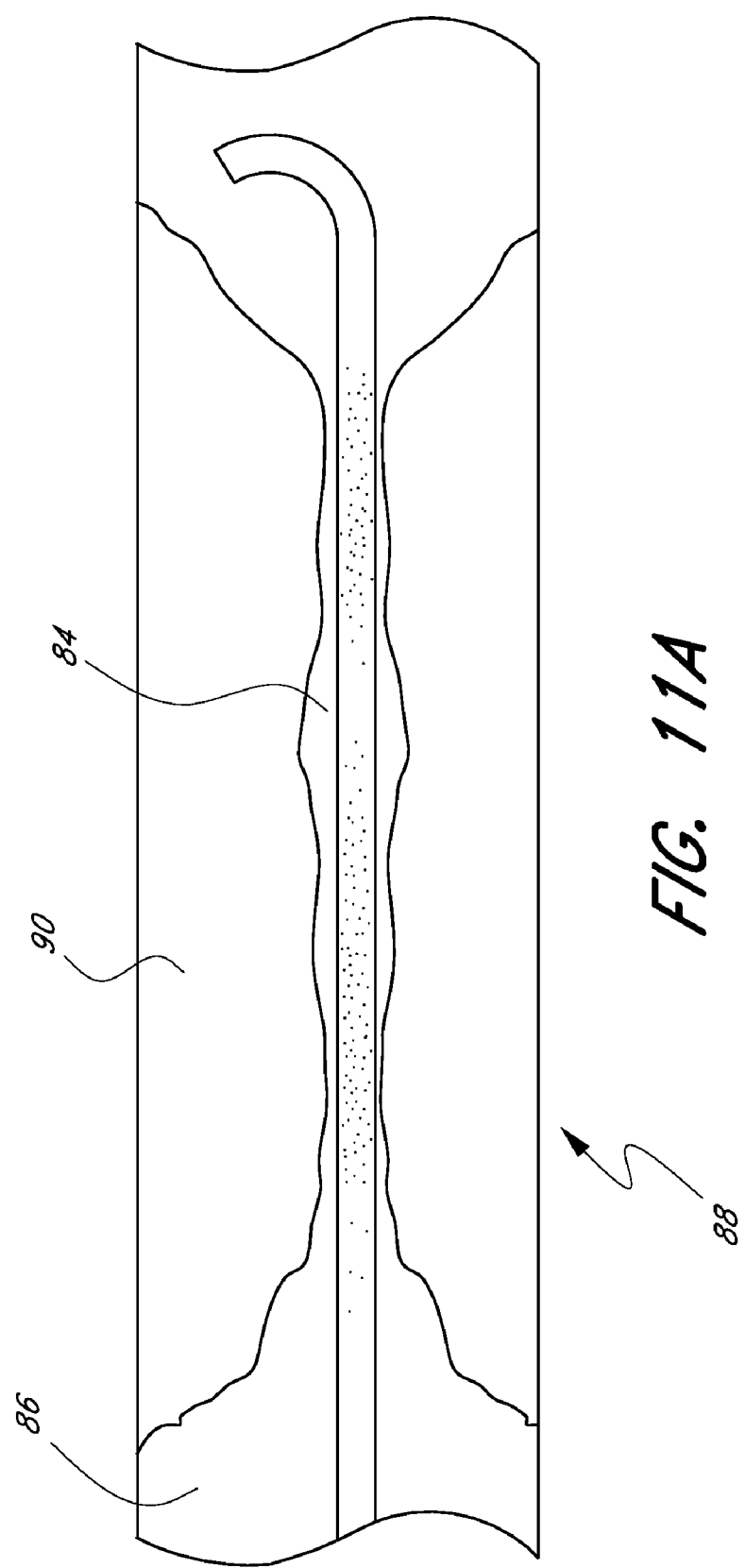
FIG. 11A is a side view of a treatment site.

FIGS. 11A through 11D illustrate a method for using the ultrasonic catheter 10. As illustrated in FIG. 11A, a guidewire 84 similar to a guidewire used in typical angioplasty procedures is directed through a patient's vessels 86 to a treatment site 88 which includes a clot 90. The guidewire 84 is directed through the clot 90. Suitable vessels 86 include, but are not limited to, the large periphery and the small cerebral blood vessels of the body. Additionally, as mentioned above, the ultrasonic catheter 10 also has utility in various imaging applications or in applications for treating and/or diagnosing other diseases in other body parts.

Figure 11B:
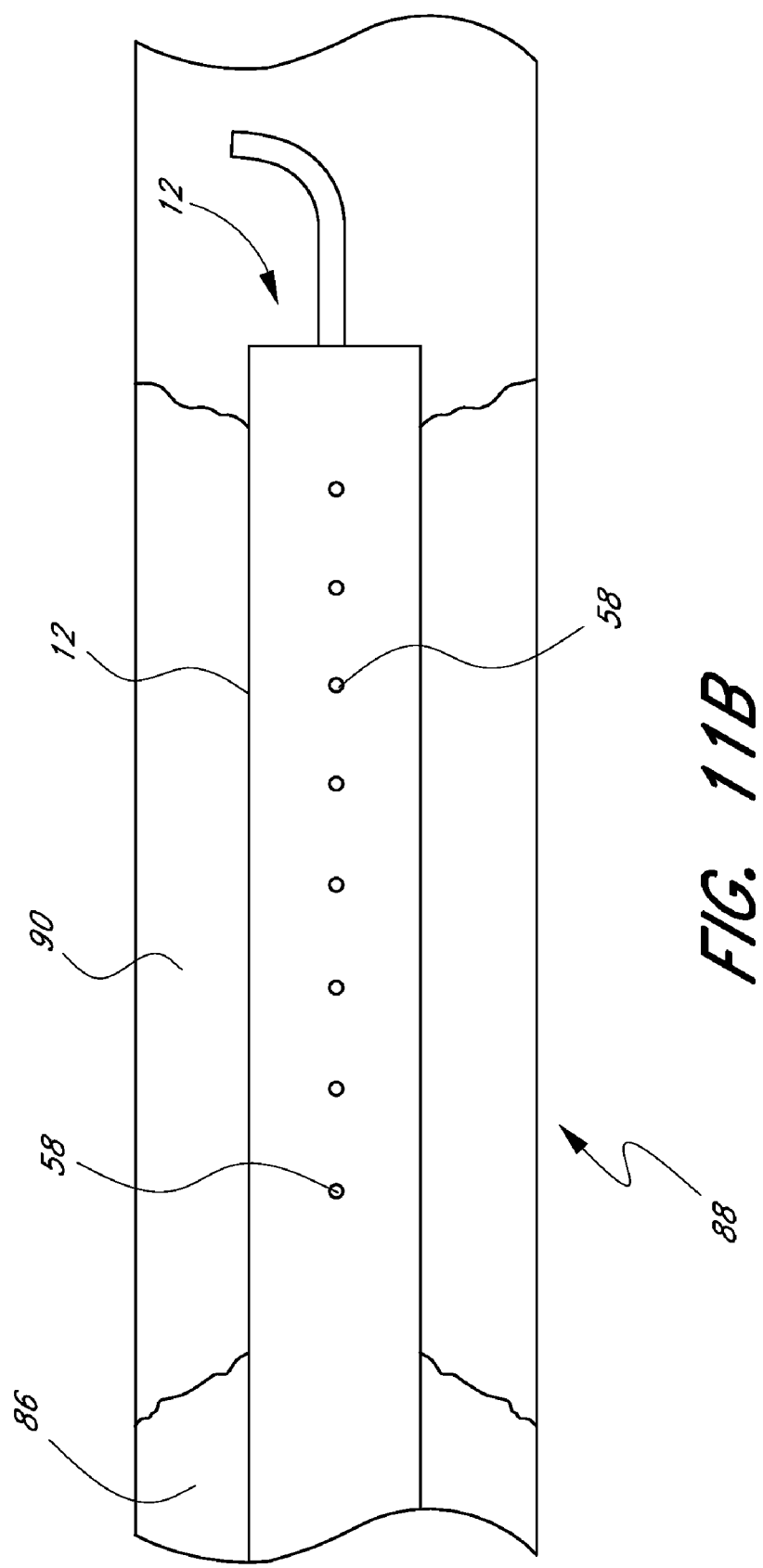
FIG. 11B is a side view of the distal end of an ultrasonic catheter positioned at the treatment site of FIG. 11A.

As illustrated in FIG. 11B, the tubular body 12 is slid over and is advanced along the guidewire 84 using conventional over-the-guidewire techniques. The tubular body 12 is advanced until the energy delivery section 18 of the tubular body 12 is positioned at the clot 90. In certain embodiments, radiopaque markers (not shown) are positioned along the energy delivery section 18 of the tubular body 12 to aid in the positioning of the tubular body 12 within the treatment site 88.

Figure 11C:
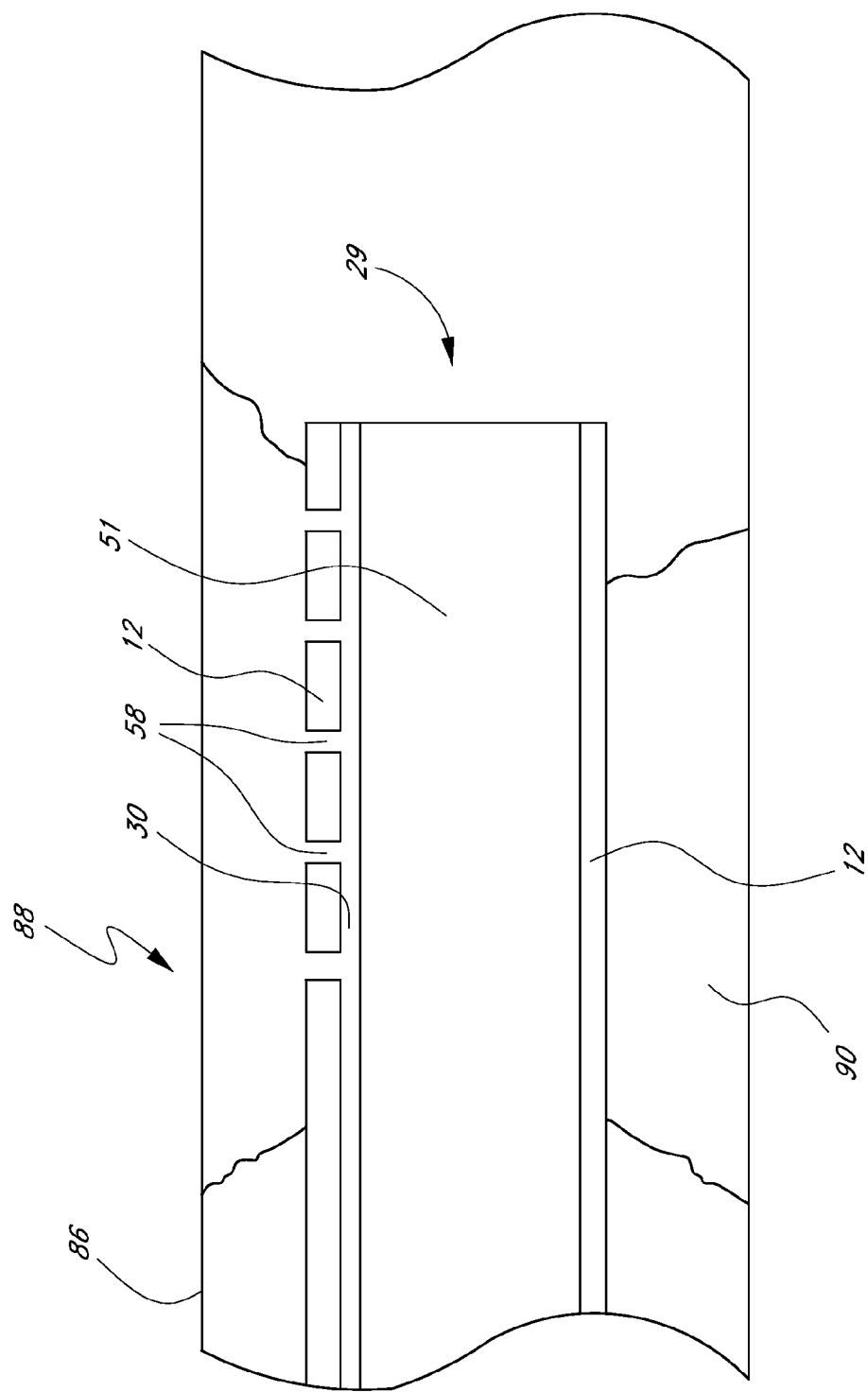
FIG. 11C is a cross-sectional view of the distal end of the ultrasonic catheter of FIG. 11B positioned at the treatment site before a treatment.

As illustrated in FIG. 11C, the guidewire 84 is then withdrawn from the tubular body 12 by pulling the guidewire 84 from the proximal region 14 of the catheter 10 while holding the tubular body 12 stationary. This leaves the tubular body 12 positioned at the treatment site 88.

Figure 11D:
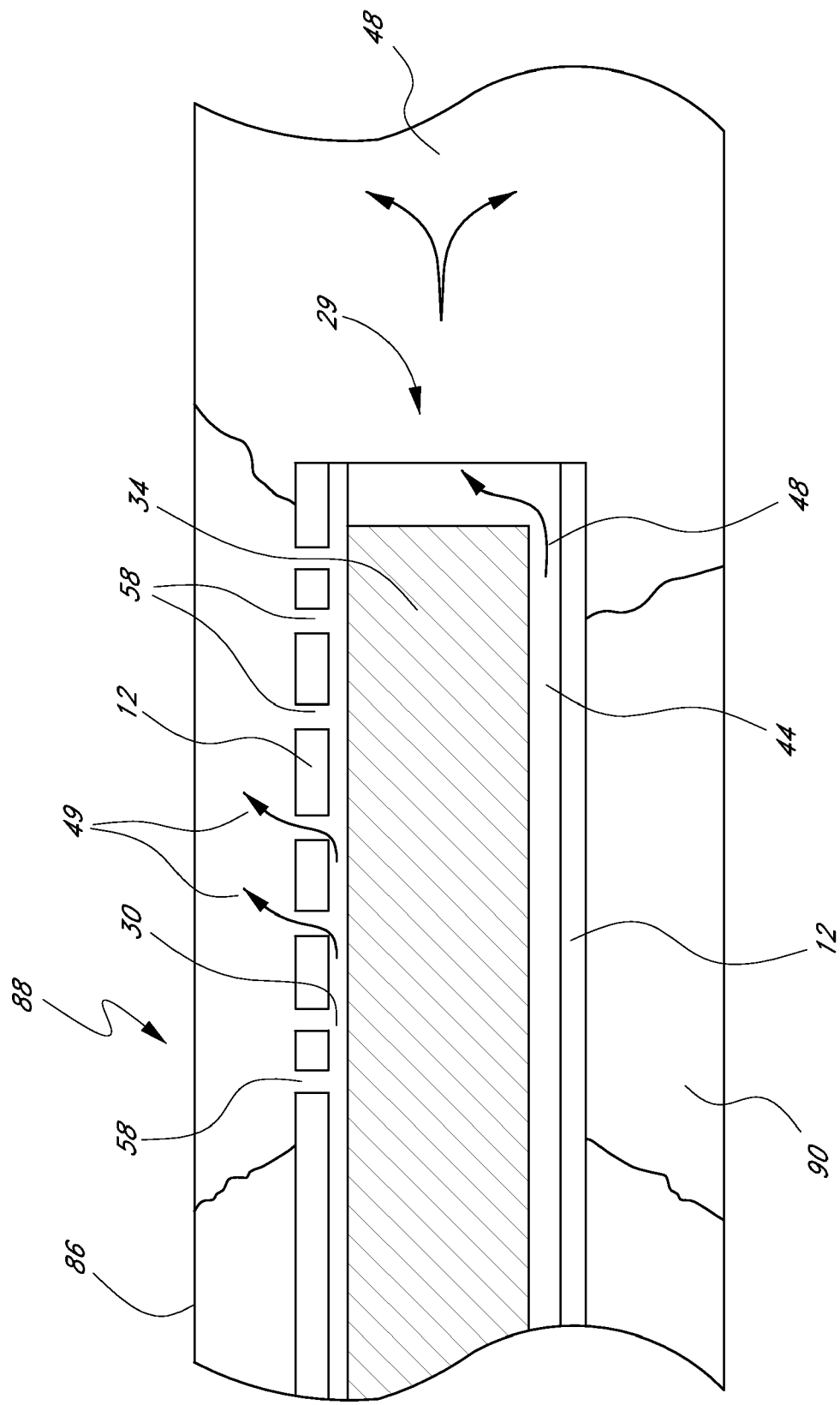
FIG. 11D is a cross-sectional view of the distal end of the ultrasonic catheter of FIG. 11C, wherein an inner core has been inserted into the tubular body to perform a treatment.

As illustrated in FIG. 11D, the inner core 34 is then inserted into the tubular body 12 until the ultrasound assembly is positioned at least partially within the energy delivery section 18 of the tubular body 12. Once the inner core 34 is properly positioned, the ultrasound assembly 42 is activated to deliver ultrasonic energy through the energy delivery section 18 to the clot 90. As described above, in one embodiment, suitable ultrasonic energy is delivered with a frequency between about 20 kHz and about 20 MHz.

In a certain embodiment, the ultrasound assembly 42 comprises sixty ultrasound radiating members 40 spaced over a length between approximately 30 cm and 50 cm. In such embodiments, the catheter 10 can be used to treat an elongate clot 90 without requiring movement of or repositioning of the catheter 10 during the treatment. However, it will be appreciated that in modified embodiments the inner core 34 can be moved or rotated within the tubular body 12 during the treatment. Such movement can be accomplished by maneuvering the proximal hub 37 of the inner core 34 while holding the backend hub 33 stationary.

Referring again to FIG. 11D, arrows 48 indicate that a cooling fluid flows through the cooling fluid lumen 44 and out the distal exit port 29. Likewise, arrows 49 indicate that a therapeutic compound flows through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the steps illustrated in FIGS. 11A through 11D can be performed in a variety of different orders than as described above. The therapeutic compound and ultrasonic energy are preferably applied until the clot 90 is partially or entirely dissolved. Once the clot 90 has been dissolved to the desired degree, the tubular body 12 and the inner core 34 are withdrawn from the treatment site 88.

Overview of a Small Vessel Ultrasound Catheter

Over the years, numerous types of ultrasound catheters have been proposed for various therapeutic purposes. However, none of the existing ultrasound catheters is well adapted for effective use within small blood vessels in the distal anatomy. For example, in one primary shortcoming, the region of the catheter on which the ultrasound assembly is located (typically along the distal end portion) is relatively rigid and therefore lacks the flexibility necessary for navigation through difficult regions of the distal anatomy. Furthermore, it has been found that it is very difficult to manufacture an ultrasound catheter having a sufficiently small diameter for use in small vessels while providing adequate pushability and torqueability. Still further, it has been found that the distal tip of an ultrasound catheter can easily damage the fragile vessels of the distal anatomy during advancement through the patient's vasculature.

Accordingly, an urgent need exists for an improved ultrasound catheter that is capable of safely and effectively navigating small blood vessels. It is also desirable that such a device be capable of delivering adequate ultrasound energy to achieve the desired therapeutic purpose. It is also desirable that such a device be capable of accessing a treatment site in fragile distal vessels in a manner that is safe for the patient and that is not unduly cumbersome. The present invention addresses these needs.

The advancement of an ultrasound catheter through a blood vessel to a treatment site can be difficult and dangerous, particularly when the treatment site is located within a small vessel in the distal region of a patient's vasculature. To reach the treatment site, it is often necessary to navigate a tortuous path around difficult bends and turns. During advancement through the vasculature, bending resistance along the distal end portion of the catheter can severely limit the ability of the catheter to make the necessary turns. Moreover, as the catheter is advanced, the distal tip of the catheter is often in contact with the inner wall of the blood vessel. The stiffness and rigidity of the distal tip of the catheter may lead to significant trauma or damage to the tissue along the inner wall of the blood vessel. As a result, advancement of an ultrasound catheter through small blood vessels can be extremely hazardous. Therefore, a need exists for an improved ultrasound catheter design that allows a physician to more easily navigate difficult turns in small blood vessels while minimizing trauma and/or damage along the inner walls of the blood vessels. To address this need, preferred embodiments of the present invention described herein provide an ultrasound catheter that is well suited for use in the treatment of small blood vessels or other body lumens having a small inner diameter.

As used herein, the term "ultrasound energy" is a broad term and is used in its ordinary sense and means, without limitation, mechanical energy transferred through pressure or compression waves with a frequency greater than about 20 kHz. In one embodiment, the waves of the ultrasound energy have a frequency between about 500 kHz and 20 MHz and in another embodiment between about 1 MHz and 3 MHz. In yet another embodiment, the waves of the ultrasound energy have a frequency of about 3 MHz.

As used herein, the term "catheter" is a broad term and is used in its ordinary sense and means, without limitation, an elongate flexible tube configured to be inserted into the body of a patient, such as, for example, a body cavity, duct or vessel.

Figure 12:
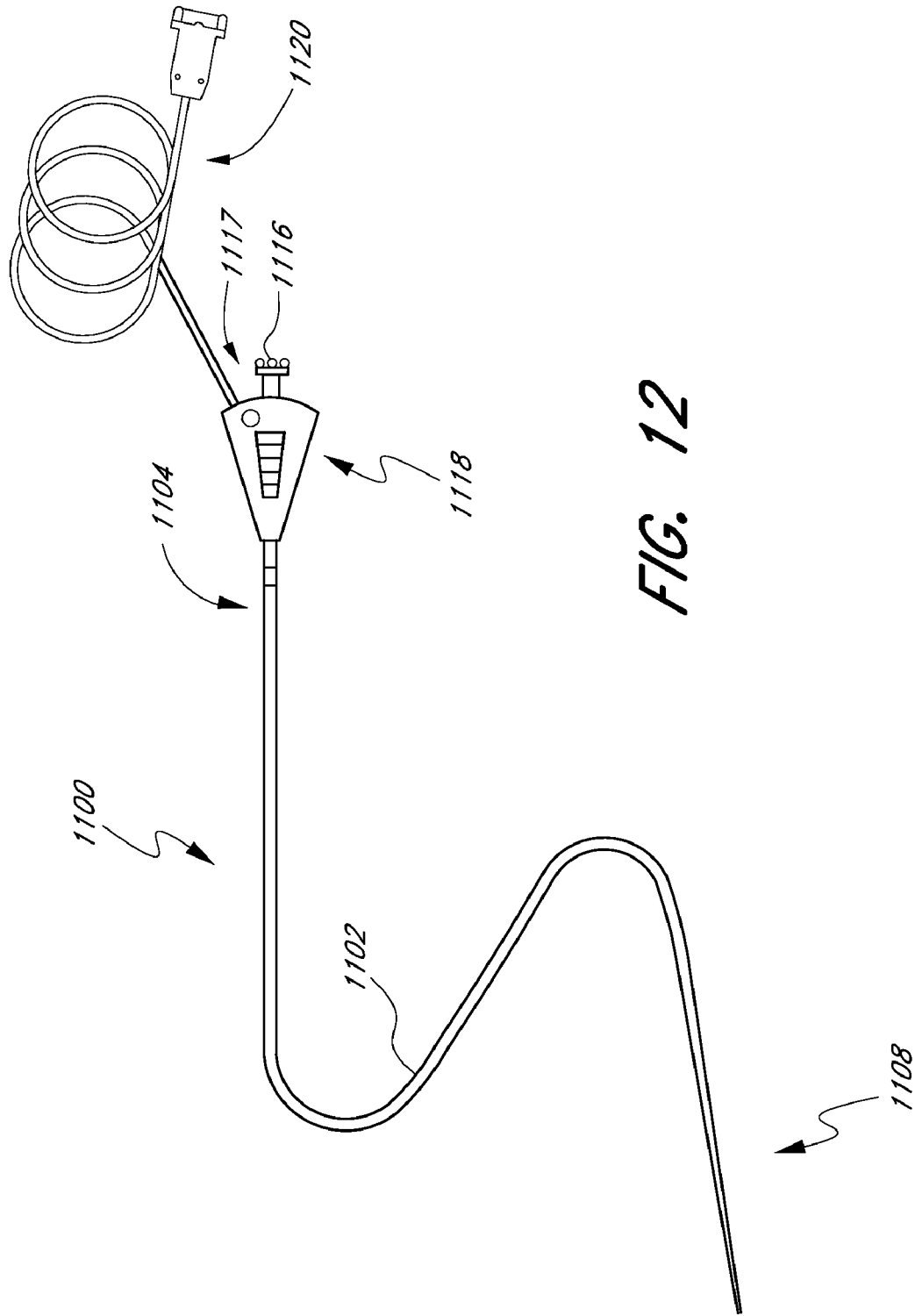
FIG. 12 is a side view of an ultrasound catheter that is particularly well suited for insertion into small blood vessels of the human body.

Referring now to FIGS. 12 through 13B, for purposes of illustration, preferred embodiments of the present invention provide an ultrasound catheter 1100 that is particularly well suited for use within small vessels of the distal anatomy, such as, for example, in the remote, small diameter, neurovasculature in the brain.

As shown in FIGS. 12 and 13A, the ultrasound catheter 1100 generally comprises a multi-component tubular body 1102 having a proximal end 1104 and a distal end 1106. The tubular body 1102 and other components of the catheter 1100 can be manufactured in accordance with any of a variety of techniques well know in the catheter manufacturing field. As discussed in more detail below, suitable material dimensions can be readily selected taking into account the natural and anatomical dimensions of the treatment site and of the desired percutaneous access site.

Preferably, the tubular body 1102 can be divided into at least three sections of varying stiffness. The first section, which preferably includes the proximal end 1104, is generally more stiff than a second section, which lies between the proximal end 1104 and the distal end 1106 of the catheter. This arrangement facilitates the movement and placement of the catheter 1102 within small vessels. The third section, which includes ultrasound radiating element 1124, is generally stiffer than the second section due to the presence of the ultrasound radiating element 1124.

In each of the embodiments described herein, the assembled ultrasound catheter preferably has sufficient structural integrity, or "pushability," to permit the catheter to be advanced through a patient's vasculature to a treatment site without buckling or kinking. In addition, the catheter has the ability to transmit torque, such that the distal portion can be rotated into a desired orientation after insertion into a patient by applying torque to the proximal end.

The elongate flexible tubular body 1102 comprises an outer sheath 1108 (see FIG. 13A) that is positioned upon an inner core 1110. In an embodiment particularly well suited for small vessels, the outer sheath 1108 comprises extruded PEBAX, PTFE, PEEK, PE, polymides, braided polymides and/or other similar materials. The distal end portion of the outer sheath 1108 is adapted for advancement through vessels having a very small diameter, such as those in the neurovasculature of the brain. Preferably, the distal end portion of the outer sheath 1108 has an outer diameter between about 2 and 5 French. More preferably, the distal end portion of the outer sheath 1108 has an outer diameter of about 2.8 French. In one preferred embodiment, the outer sheath 1108 has an axial length of approximately 150 centimeters.

In other embodiments, the outer sheath 1108 can be formed from a braided tubing formed of, by way of example, high or low density polyethylenes, urethanes, nylons, and the like. Such an embodiment enhances the flexibility of the tubular body 1102. For enhanced pushability and torqueability, the outer sheath 1108 may be formed with a variable stiffness from the proximal to the distal end. To achieve this, a stiffening member may be included along the proximal end of the tubular body 1102.

The inner core 1110 defines, at least in part, a delivery lumen 1112, which preferably extends longitudinally along the entire length of the catheter 1100. The delivery lumen 1112 has a distal exit port 1114 and a proximal access port 1116. Referring again to FIG. 12, the proximal access port 1116 is defined by drug inlet port 1117 of a back end hub 1118, which is attached to the proximal end 1104 of the other sheath 1108. The illustrated back end hub 1118 is preferably attached to a control box connector 1120, the utility of which will be described in more detail below.

The delivery lumen 1112 is preferably configured to receive a guide wire (not shown). Preferably, the guidewire has a diameter of approximately 0.008 to 0.012 inches. More preferably, the guidewire has a diameter of about 0.010 inches. The inner core 1110 is preferably formed from polymide or a similar material which, in some embodiments, can be braided to increase the flexibility of the tubular body 1102.

With particular reference to FIGS. 13A and 13B, the distal end 1106 of the catheter 1102 preferably includes the ultrasound radiating element 1124. In the illustrated embodiment, the ultrasound radiating element 1124 comprises an ultrasound transducer, which converts, for example, electrical energy into ultrasound energy. In a modified embodiment, the ultrasound energy can be generated by an ultrasound transducer that is remote from the ultrasound radiating element 1124 and the ultrasound energy can be transmitted via, for example, a wire to the ultrasound radiating element 1124.

In the embodiment illustrated in FIGS. 13A and 13B, the ultrasound radiating element 1124 is configured as a hollow cylinder. As such, the inner core 1110 can extend through the lumen of the ultrasound radiating element 1124. The ultrasound radiating element 1124 can be secured to the inner core 1110 in any suitable manner, such as with an adhesive. A potting material may also be used to further secure the mounting of the ultrasound radiating element along the central core.

In other embodiments, the ultrasound radiating element 1124 can be configured with a different shape without departing from the scope of the invention. For example, the ultrasound radiating element may take the form of a solid rod, a disk, a solid rectangle or a thin block. Still further, the ultrasound radiating element 1124 may comprise a plurality of smaller ultrasound radiating elements. The illustrated arrangement is the generally preferred configuration because it provides for enhanced cooling of the ultrasound radiating element 1124. For example, in one preferred embodiment, a drug solution can be delivered through the delivery lumen 1112. As the drug solution passes through the lumen of the ultrasound radiating element, the drug solution may advantageously provide a heat sink for removing excess heat generated by the ultrasound radiating element 1124. In another embodiment, a return path can be formed in the space 1138 between the outer sheath and the inner core such that coolant from a coolant system can be directed through the space 1138.

The ultrasound radiating element 1124 is preferably selected to produce ultrasound energy in a frequency range that is well suited for the particular application. Suitable frequencies of ultrasound energy for the applications described herein include, but are not limited to, from about 20 kHz to about 20 MHz. In one embodiment, the frequency is between about 500 kHz and 20 MHz and in another embodiment from about 1 MHz and about 3 MHz. In yet another embodiment, the ultrasound energy has a frequency of about 3 MHz.

As mentioned above, in the illustrated embodiment, ultrasound energy is generated from electrical power supplied to the ultrasound radiating element 1124. The electrical power can be supplied through the controller box connector 1120, which is connected to a pair wires 1126, 1128 that extend through the catheter body 1102. The electrical wires 1126, 1128 can be secured to the inner core 1110, lay along the inner core 1110 and/or extend freely in the space between the inner core 1110 and the outer sheath 1108. In the illustrated arrangement, the first wire 1126 is connected to the hollow center of the ultrasound radiating element 1124 while the second wire 1128 is connected to the outer periphery of the ultrasound radiating element 1124. The ultrasound radiating element 1124 is preferably, but is not limited to, a transducer formed of a piezoelectric ceramic oscillator or a similar material.

With continued reference to FIGS. 13A and 13B, the distal end 1104 of the catheter 1100 preferably includes a sleeve 1130, which is generally positioned about the ultrasound radiating element 1124. The sleeve 1130 is preferably constructed from a material that readily transmits ultrasound energy. Suitable materials for the sleeve 1130 include, but are not limited to, polyolefins, polyimides, polyester and other materials having a relatively low absorbance to ultrasound energy. Low ultrasound absorbance materials are materials that readily transmit ultrasound energy with minimal absorption of the ultrasound energy. The proximal end of the sleeve 1130 can be attached to the outer sheath 1108 with an adhesive 1132. To improve the bonding of the adhesive 1132 to the outer sheath 1108, a shoulder 1127 or notch may be formed in the outer sheath for attachment of the adhesive thereto. Preferably, the outer sheath 1108 and the sleeve 1130 have substantially the same outer diameter.

In a similar manner, the distal end of the sleeve 1130 can be attached to a tip 1134. In the illustrated arrangement, the tip 1134 is also attached to the distal end of the inner core 1110. Preferably, the tip is between about 0.5 and 4.0 millimeters in length. More preferably, the tip is about 2.0 millimeters in length. As illustrated, the tip is preferably rounded in shape to reduce trauma or damage to tissue along the inner wall of a blood vessel or other body structure during advancement toward a treatment site.

With continued reference to FIG. 13B, the catheter 1100 preferably includes at least one temperature sensor 1136 along the distal end 1106. The temperature sensor 1136 is preferably located on or near the ultrasound radiating element 1124. Suitable temperature sensors include but are not limited to, diodes, thermistors, thermocouples, resistance temperature detectors (RTDs), and fiber optic temperature sensors that used thermochromic liquid crystals. The temperature sensor is preferably operatively connected to a control box (not shown) through a control wire, which extends through the catheter body 1102 and back end hub 1118 and is operatively connected to a control box through the control box connector 1120. The control box preferably includes a feedback control system having the ability to monitor and control the power, voltage, current and phase supplied to the ultrasound radiating element. In this manner, the temperature along the relevant region of the catheter can be monitored and controlled for optimal performance. Details of the control box can be found in Assignee's co-pending provisional application entitled CONTROL POD FOR ULTRASONIC CATHETER, Application Ser. No. 60/336,630, filed Dec. 3, 2001, which is incorporated by reference in its entirety.

In one exemplary application of the ultrasound catheter 1100 described above, the apparatus may be used to remove a thrombotic occlusion from a small blood vessel. In one preferred method of use, a free end of a guidewire is percutaneously inserted into the patient's vasculature at a suitable first puncture site. The guidewire is advanced through the vasculature toward a treatment site wherein the blood vessel is occluded by the thrombus. The guidewire wire is preferably then directed through the thrombus.

After advancing the guidewire to the treatment site, the catheter 1100 is thereafter percutaneously inserted into the vasculature through the first puncture site and is advanced along the guidewire towards the treatment site using traditional over-the-guidewire techniques. The catheter 1100 is advanced until the distal end 1106 of the catheter 1100 is positioned at or within the occlusion. The distal end 1106 of the catheter 1100 may include one or more radiopaque markers (not shown) to aid in positioning the distal end 1106 within the treatment site.

After placing the catheter, the guidewire can then be withdrawn from the delivery lumen 1112. A drug solution source (not shown), such as a syringe with a Luer fitting, is attached to the drug inlet port 1117 and the controller box connector 1120 is connected to the control box. As such, the drug solution can be delivered through the delivery lumen 1112 and out the distal access port 1114 to the thrombus. Suitable drug solutions for treating a thrombus include, but are not limited to, an aqueous solution containing Heparin, Uronkinase, Streptokinase, and/or tissue Plasminogen Activator (TPA).

The ultrasound radiating element 1124 is activated to emit ultrasound energy from the distal end 1106 of the catheter 1100. As mentioned above, suitable frequencies for the ultrasound radiating element 1124 include, but are not limited to, from about 20 kHz to about 20 MHz. In one embodiment, the frequency is between about 500 kHz and 20 MHz and in another embodiment between about 1 MHz and 3 MHz. In yet another embodiment, the ultrasound energy is emitted at a frequency of about 3 MHz. The drug solution and ultrasound energy are applied until the thrombus is partially or entirely dissolved. Once the thrombus has been dissolved to the desired degree, the catheter 1100 is withdrawn from the treatment site.

Overview of Ultrasonic Catheter Power Control

In embodiments wherein the ultrasound radiating member is a PZT transducer, the transducer is typically excited by specific electrical parameters that causes it to vibrate ultrasonically. Suitable frequencies for the ultrasound radiating member include, but are not limited to, from about 20 kHz to less than about 20 MHz, inclusive. In one embodiment, the frequency is between about 500 kHz and 20 MHz, inclusive, and in another embodiment is between about 1 MHz and 3 MHz, inclusive. In yet another embodiment, the sound waves have a frequency of about 3 MHz. Within these frequency ranges, Applicant has determined that the in vivo production of cavitation and/or the enhancement of the biological effect of drugs, medication and other therapeutic compounds caused by the ultrasonic vibrations can be further enhanced by using particular electrical parameters to produce the frequencies described above. In particular, Applicant has measured the dependence of enhanced thrombolytic action that results from the combination of a lytic drug and ultrasonic vibrations using the electrical parameters described herein.

In one embodiment, the PZT transducer is operated using pulses, or modulated electrical drive power, instead of continuous drive power. That is, the duty cycle for exciting the transducers is chosen to avoid excessive tissue heating. Applicant believes that the clinical biological effect (that is, the enhancement of the therapeutic effects of a drug, medication, pharmacological agent, or other therapeutic compound) created by ultrasonic vibration decays after the vibration stops, rather than stopping immediately. That is, the biological effect continues after delivery of ultrasonic energy has ceased. For example, Applicant has conducted numerous experiments that indicate that the clinical biological effect of enhanced thrombolysis continues after delivery of ultrasonic energy has ceased. Therefore, the power amplitude of the ultrasonic vibrations can be maximized to create the greatest clinical biological effect, while the duty cycle of the ultrasonic vibrations is reduced to avoid unnecessary heating. Both amplitude and duration are preferably constrained to avoid damaging the transducers.

For example, in one embodiment, the time average power is preferably between about 0.1 watts and 2 watts and is more preferably between about 0.5 watts and 1.5 watts. In certain preferred embodiments, the time average power is approximately 0.6 watts or 1.2 watts. The duty cycle is preferably between about 1% and 50% and is more preferably between about 5% and 25%. In certain preferred embodiments, the duty cycle is approximately 7.5% or 15%. The pulse averaged power is preferably between about 0.1 watts and 20 watts and is more preferably between approximately 5 watts and 20 watts. In certain preferred embodiments, the pulse averaged power is approximately 8 watts or 16 watts. The amplitude during each pulse can be constant or varied.

In addition to measuring the power delivered to the treatment site as a time average power or a pulse average power as described above, the power delivered can be measured in an intensity per unit area (for example, watts per square inch or watts per square centimeter), which may also be referred to as the in situ intensity at the energy radiating surface. In such a measurement, the output power of the ultrasound radiating member is projected onto the outer surface of the catheter, which is where the emitted ultrasonic energy first encounters biological material (such as clot material in a patient's vasculature). For example, for an arbitrarily-shaped ultrasound radiating member that emits a time average power P and that has a length h that is positioned within a catheter having an outer diameter d, the in situ intensity at the energy radiating surface I is given by $$I = \frac{P}{\pi d h}.$$

The following table provides illustrative examples of area power intensity calculations for typical ultrasonic catheter parameters; other parameters can be used in other embodiments

| time average power P (watts) | catheter outer diameter d | ultrasound radiating member length h | in situ intensity at the energy radiating surface I |
|---|---|---|---|
| 0.5 | 0.037 in | 0.080 in | 53.8 watts in$^{-2}$ |
| 0.6 | 0.037 in | 0.080 in | 64.5 watts in$^{-2}$ |
| 0.6 | 0.071 in | 0.080 in | 33.6 watts in$^{-2}$ |
| 1.5 | 0.071 in | 0.080 in | 84.1 watts in$^{-2}$ |
| 0.5 | 0.094 cm | 0.203 cm | 8.34 watts cm$^{-2}$ |
| 0.6 | 0.094 cm | 0.203 cm | 10.0 watts cm$^{-2}$ |
| 1.2 | 0.180 cm | 0.203 cm | 10.5 watts cm$^{-2}$ |
| 1.5 | 0.180 cm | 0.203 cm | 13.1 watts cm$^{-2}$ |

The biological effect of drugs, medication and other pharmacological agents can also be enhanced by using particular pulse repetition rates and/or particular pulse durations. For example, in one embodiment, the pulse repetition rate is preferably between about 5 Hz and 150 Hz and is more preferably between about 10 Hz and 50 Hz. In certain preferred embodiments, the pulse repetition rate is approximately 30 Hz. The pulse duration is preferably between about 1 millisecond and 50 milliseconds and more preferably between about 1 millisecond and 25 milliseconds. In certain preferred embodiments, the pulse duration is approximately 2.5 milliseconds or 5 milliseconds.

The PZT transducer used with the electrical parameters described herein preferably has an acoustic efficiency greater than 50% and more preferably greater than 75%. The transducer may be formed a variety of shapes, such as, for example, cylindrical (solid or hollow), flat, bar, triangular, and so forth. The length of the transducer is preferably between about 0.1 centimeters and about 0.5 centimeters. The thickness or diameter of the transducer is preferably between about 0.02 centimeters and about 0.2 centimeters.

Table A describes one particular modulation pattern that has been optimized for a specific set of conditions. This "A" protocol is characterized by having an average power of approximately 0.6 watts, a duty cycle of approximately 7.5%, a pulse repetition rate of approximately 30 Hz, a pulse average electrical power of approximately 8 watts and a pulse duration of approximately 2.5 milliseconds. This "A" protocol produces an in situ intensity at the energy radiating surface of 64.5 watts in$^{-2}$ when used with a smaller diameter catheter. This "A" protocol produces an in situ intensity at the energy radiating surface of 33.6 watts in$^{-2}$ when used with a larger diameter catheter. This "A" protocol is intended to enhance the acoustic output of a catheter comprising ultrasonic transducers. In particular, enhancement is indicated by enhanced clot lysis with reduced or acceptable heat production in the catheter.

Tables B and C illustrate two modified embodiments of the modulation pattern of Table A. In Table B, the average electrical power, the pulse average electrical power, and the in situ intensity at the energy radiating surface are approximately twice that of Table A. In Table C, the duty cycle and the pulse duration are approximately twice that of Table A

TABLE A

| Parameter | Approximate Value |
|---|---|
| Time-average Electrical Power | 0.6 watts |
| Pulse-average Electrical Power | 8.0 watts |
| Duty Cycle | 7.5 % |
| Pulse Duration | 2.5 milliseconds |
| Pulse Repetition Rate | 30 Hz |

Table A illustrates that, in one embodiment, a catheter having an outer diameter of 0.037 inches and including one or more transducers of length 0.080 inches will deliver an in situ intensity at the energy radiating surface of 64.5 watts in$^{-2}$. Likewise, in another embodiment, a catheter having an outer diameter of 0.071 inches and including one or more transducers of length 0.080 inches will deliver an in situ intensity at the energy radiating surface of 33.6 watts in$^{-2}$.

TABLE B

| Parameter | Approximate Value |
| --- | --- |
| Time-average Electrical Power | 1.2 watts |
| Pulse-average Electrical Power | 16.0 watts |
| Duty Cycle | 7.5% |
| Pulse Duration | 2.5 milliseconds |
| Pulse Repetition Rate | 30 Hz |

Table B illustrates that, in one embodiment, a catheter having an outer diameter of 0.037 inches and including one or more transducers of length 0.080 inches will deliver an in situ intensity at the energy radiating surface of 129 watts in$^{-2}$. Likewise, in another embodiment, a catheter having an outer diameter of 0.071 inches and including one or more transducers of length 0.080 inches will deliver an in situ intensity at the energy radiating surface of 67.2 watts in$^{-2}$.

TABLE C

| Parameter | Approximate Value |
| --- | --- |
| Time-average Electrical Power | 1.2 watts |
| Pulse-average Electrical Power | 8.0 watts |
| Duty Cycle | 15.0% |
| Pulse Duration | 5 milliseconds |
| Pulse Repetition Rate | 30 Hz |

Table B illustrates that, in one embodiment, a catheter having an outer diameter of 0.037 inches and including one or more transducers of length 0.080 inches will deliver an in situ intensity at the energy radiating surface of 129 watts in$^{-2}$. Likewise, in another embodiment, a catheter having an outer diameter of 0.071 inches and including one or more transducers of length 0.080 inches will deliver an in situ intensity at the energy radiating surface of 67.2 watts in$^{-2}$.

It should be appreciated that, although the embodiments described above are described in the context of a PZT transducer, certain features and aspects may be applied to an ultrasonic radiating element that is not a PZT transducer. That is, operating the ultrasound radiating member using pulses, or modulated electrical drive power, instead of continuous drive power may have utility outside the context of a PZT transducer. Such embodiments also seek to maximize clinical biological effect avoiding unnecessary heating.

CONCLUSION

While the foregoing detailed description has described several embodiments of the apparatus and methods of the present invention, it is to be understood that the above description is illustrative only and not limiting of the disclosed invention. It will be appreciated that the specific dimensions of the various catheters and guidewires can differ from those described above, and that the methods described can be used within any biological conduit within the body and remain within the scope of the present invention. Thus, the invention is to be limited only by the claims which follow.

We claim:

1. A method of treating an occlusion at a treatment site within a patient's vasculature comprising:
    providing an ultrasonic catheter having a distal region, a proximal region opposite the distal region, a fluid delivery lumen having at least one opening in the distal region, and an ultrasound radiating member positioned within the distal region;
    positioning the ultrasonic catheter at the treatment site, such that at least a portion of the distal region is within the occlusion;
    passing a therapeutic compound through the fluid delivery lumen such that the therapeutic compound is delivered to the treatment site; and
    emitting ultrasonic energy from the ultrasound radiating member operating at a frequency of between 500 kHz and about 20 MHz, wherein the emitted ultrasonic energy has
        an amplitude that is periodically varied between a low amplitude and a high amplitude,
        a pulse average power exclusive of the low amplitude periods of between approximately 0.01 watts and approximately 20 watts,
        a high amplitude pulse duration of between approximately 1 millisecond and approximately 50 milliseconds,
        a high amplitude pulse repetition rate of between approximately 5 hertz and approximately 150 hertz, and
        an in situ intensity at an energy radiating surface of between approximately 20 watts in$^{-2}$ and approximately 90 watts in$^{-2}$.

2. The method of claim 1, wherein the emitted ultrasonic energy has an in situ intensity at the energy radiating surface of between approximately 30 watts in$^{-2}$ and approximately 65 watts in$^{-2}$.

3. The method of claim 1, wherein the emitted ultrasonic energy has a time average power inclusive of the low amplitude and the high amplitude periods of between approximately 0.1 watts and approximately 2.0 watts.

4. The method of claim 3, wherein the emitted ultrasonic energy has a time average power inclusive of the low amplitude and the high amplitude periods of between approximately 0.6 watts and approximately 1.2 watts.

5. The method of claim 1, wherein the emitted ultrasonic energy has a pulse average power exclusive of the low amplitude periods of between approximately 8 watts and approximately 16 watts.

6. The method of claim 1, wherein the emitted ultrasonic energy has a duty cycle of between approximately 1% and approximately 50%.

7. The method of claim 6, wherein the emitted ultrasonic energy has a duty cycle of between approximately 7.5% and approximately 15%.

8. The method of claim 1, wherein the emitted ultrasonic energy has a high amplitude pulse duration of between approximately 2.5 milliseconds and approximately 5 milliseconds.

9. The method of claim 1, wherein the ultrasound radiating member is a PZT transducer.

10. The method of claim 1, further comprising monitoring a temperature at the treatment site.

11. The method of claim 10, further comprising adjusting a time average power inclusive of the low amplitude and the high amplitude periods in response to the temperature measured at the treatment site.

* * * * *